(12) United States Patent
Zeng et al.

(10) Patent No.: US 12,419,508 B2
(45) Date of Patent: *Sep. 23, 2025

(54) OPTICAL OBSERVATION EQUIPMENT AND METHOD FOR IDENTIFYING FORMING PROCESS OF MALIGNANT TUMOR AND ENDOSCOPE

(71) Applicants: Kun Zeng, Shanghai (CN); Guozheng Yan, Shanghai (CN); Zhenfen Yu, Shanghai (CN)

(72) Inventors: Kun Zeng, Shanghai (CN); Guozheng Yan, Shanghai (CN); Zhenfen Yu, Shanghai (CN); Wen Liu, Shanghai (CN); Xiuzhang Wang, Shanghai (CN); Zhiwu Wang, Shanghai (CN); Dasheng Liu, Shanghai (CN); Pingping Jiang, Shanghai (CN)

(73) Assignees: Kun Zeng, Shanghai (CN); Guozheng Yan, Shanghai (CN); Zhenfen Yu, Shanghai (CN)

( * ) Notice: Subject to any disclaimer, the term of this patent is extended or adjusted under 35 U.S.C. 154(b) by 975 days.

This patent is subject to a terminal disclaimer.

(21) Appl. No.: 17/178,980

(22) Filed: Feb. 18, 2021

(65) Prior Publication Data

US 2021/0169317 A1 Jun. 10, 2021

Related U.S. Application Data

(63) Continuation-in-part of application No. 15/312,476, filed as application No. PCT/CN2015/078924 on May 14, 2015, now Pat. No. 10,952,618.

(30) Foreign Application Priority Data

May 20, 2014 (CN) .......................... 201410217638.0

(51) Int. Cl.
*A61B 1/04* (2006.01)
*A61B 1/00* (2006.01)
(Continued)

(52) U.S. Cl.
CPC ........ *A61B 1/0638* (2013.01); *A61B 1/00188* (2013.01); *A61B 1/043* (2013.01);
(Continued)

(58) Field of Classification Search
CPC ............................. A61B 1/043; A61B 5/0071
See application file for complete search history.

(56) References Cited

U.S. PATENT DOCUMENTS 5,456,260 A 10/1995 Kollias et al.
5,697,373 A 12/1997 Richards-Kortum et al.
(Continued)

FOREIGN PATENT DOCUMENTS

CN 1164989 11/1997
CN 1493250 5/2004
(Continued)

OTHER PUBLICATIONS

International Search Report, issued in the International application No. PCT/CN2015/078924, dated Aug. 5, 2015 (7 pages).

*Primary Examiner* — Amelie R Davis
(74) *Attorney, Agent, or Firm* — HSML P. C.

(57) ABSTRACT

Disclosed is optical observation equipment for identifying the forming process of a malignant tumor, which is provided with a receiving space and a transparent front end. The optical observation equipment comprises: a light-guide fiber, a laser emitter, a focusing device, a white light emitter, an image sensor, a high gain amplifier and an encoding and emitting device, wherein the light-guide fiber extends to the transparent front end from the receiving space; the laser emitter emits laser with a wavelength of 340 nm±20 nm and
(Continued)

an energy of 0.3~0.5 mj/m² in a pulsing mode; the focusing device is coupled to the output end of the laser emitter and used for focusing the laser to the input end of the light-guide fiber; the white light emitter is used for emitting white light, and the white light is guided into the input end of the light-guide fiber, wherein the laser emitter and the white light emitter are alternately turned on; the image sensor is used for acquiring an image of an area irradiated by light emitted from the output end of the light-guide fiber and converting a light signal into an electric signal; the high gain amplifier is coupled to the image sensor and is used for amplifying the electric signal generated by the image sensor; and the encoding and emitting device is coupled to the high gain amplifier and is used for encoding the signal output by the high gain amplifier and emitting the encoded signal.

11 Claims, 5 Drawing Sheets

(51) Int. Cl.
*A61B 1/05* (2006.01)
*A61B 1/06* (2006.01)
*A61B 5/00* (2006.01)

(52) U.S. Cl.
CPC .............. *A61B 1/05* (2013.01); *A61B 1/0684* (2013.01); *A61B 5/0071* (2013.01)

(56) References Cited

U.S. PATENT DOCUMENTS

| | | | |
|---|---|---|---|
| 9,123,614 | B2 | 9/2015 | Graff et al. |
| 2002/0013512 | A1 | 1/2002 | Sendai et al. |
| 2003/0176768 | A1 | 9/2003 | Gono et al. |
| 2008/0161699 | A1 | 7/2008 | Zeng et al. |
| 2010/0249607 | A1 | 9/2010 | Yu et al. |
| 2012/0016230 | A1 | 1/2012 | Kishima et al. |
| 2012/0182754 | A1 | 7/2012 | Wolter |
| 2013/0079645 | A1 | 3/2013 | Amirana et al. |
| 2015/0297086 | A1 | 10/2015 | Hong et al. |
| 2016/0040854 | A1 | 2/2016 | Zhang |
| 2017/0071472 | A1* | 3/2017 | Zeng .................... A61B 5/7275 |

FOREIGN PATENT DOCUMENTS

| | | |
|---|---|---|
| CN | 103705200 | 4/2014 |
| CN | 103989459 | 8/2014 |
| EP | 1568333 | 8/2005 |

* cited by examiner

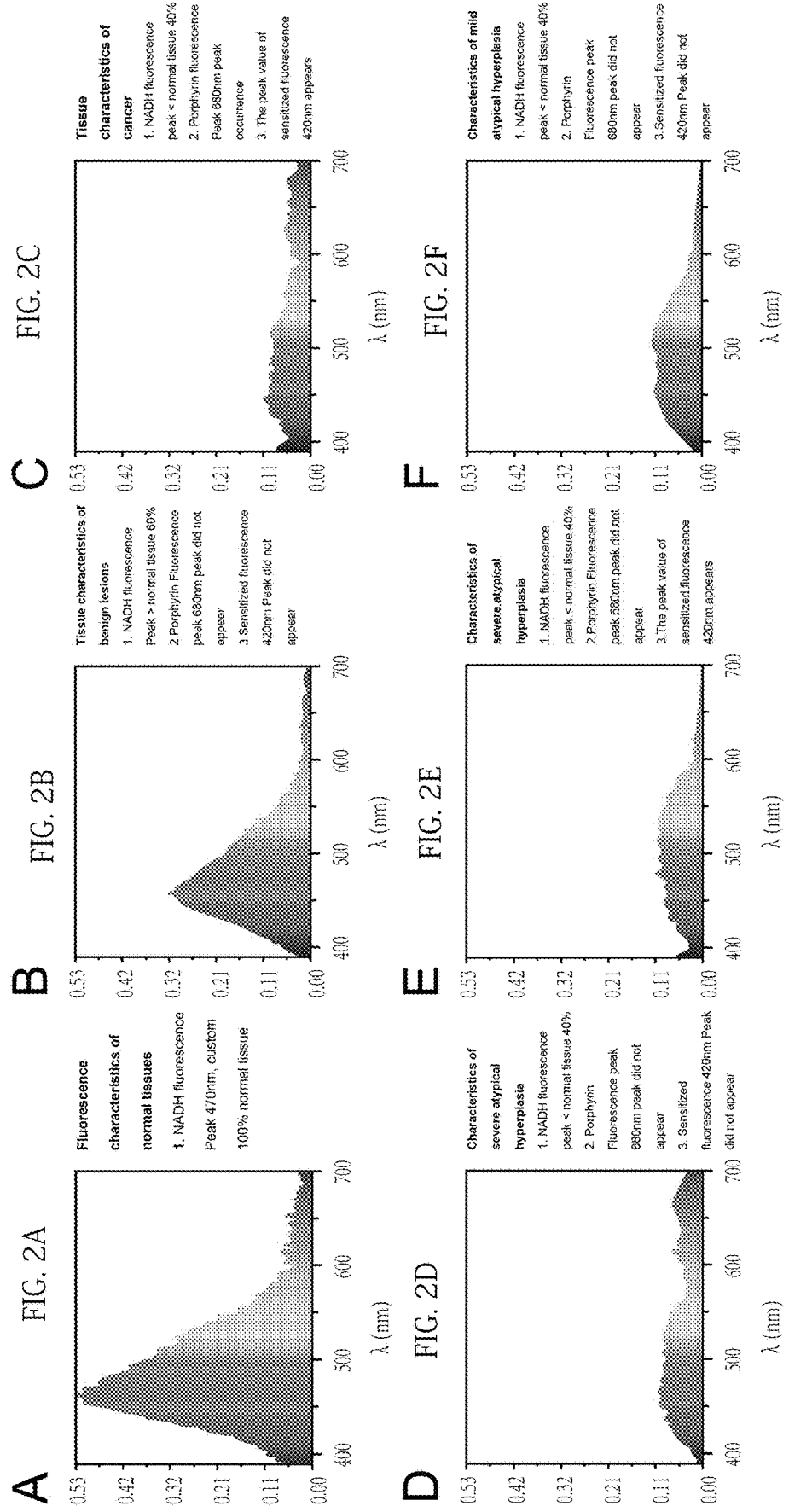

NADH fluorescence spectrum curves of normal human epithelial tissues

OPTICAL OBSERVATION EQUIPMENT AND METHOD FOR IDENTIFYING FORMING PROCESS OF MALIGNANT TUMOR AND ENDOSCOPE

TECHNICAL FIELD

The present invention relates to the field of medical devices, more particularly relates to equipment for identifying tissues using fluorescence excited by laser irradiation.

TECHNICAL BACKGROUND

Tumors, especially malignant tumors have becoming the greatest enemy of human health. Reducing "morbidity and mortality of malignant tumor" is universally recognized as the problem for tumor. To solve this problem, scientific guidance and correct strategies are needed. "Early detection, early diagnosis and early treatment of malignant tumors" is a scientific and correct strategy. The intention of the strategy is to actively protect and control malignant tumors, rather than passively treat the malignant tumors after they are formed. Once malignant tumors are formed, it is difficult to reverse and progress quickly, meanwhile during the treatment of a tumor after the malignant tumor is formed, a large number of normal healthy cells are also killed, which significantly reduces the success of treatment and the quality of patient's life. Therefore the efficacy of passive treatment after the formation of malignant tumor is very limited, which is difficult to achieve desired results.

One of the main reasons of the high incidence of cancer in the world is that diagnostic medicine still remains in the stage of morphological diagnosis method. Morphological diagnosis methods mainly depend on the experience of physicians. Although various equipments in modern technology are used, such as endoscope, confocal laser scanning endoscope (CLE), X ray, molybdenum target, ultrasonic imaging (type-B ultrasonic), CT, and nuclear magnetic resonance (MRI), the function of these equipments is only to obtain an image. Morphological diagnosis methods are used in the process of diagnosis according to the image, and the diagnosis is based on the physician's own clinical experience. After observing the video or image provided by the above diagnostic instruments, diagnosis is made according to the morphology of image, such as bulge shape, and sunken shape, irregular particles, and island mucosa. For the formed malignant tumor, its morphological characteristics are obvious. However, at the early stage of tumor, especially when the locus of malignant tumor is smaller than 5 mm, the morphological characteristics are not obvious, and some tumors even look the same as a normal, healthy tissue. In this case, diagnosis and identification can not be morphologically carried out only relying on the physician's experience, even if a clear image is obtained by the above instruments. Therapeutically, when the locus of malignant tumor is smaller than 5 mm, it belongs to micro invasive malignant tumors or is in the stage of precancerous lesion, and if timely treated, the cure rate and survival rate of malignant tumors will be significantly improved. One-third of them can be reversed through intervention, one-third of them can be cured and recovered, and one-third of them can be treated thereby prolonging life of patients.

At present, the main direction of the development of diagnostic instruments for malignant tumor, is to continuously improve the level of imaging, but the principle and basis for diagnosis is still morphological principle. After obtaining high-resolution images, physician's experience is still needed to make a judgment. According to the above analysis, such instruments can indeed improve the diagnosis rate of malignant tumors after middle stage, and the lifecycle of patients with malignant tumor can be extended to some extent. However, after the mid-term, it is difficult to reverse and cure the malignant tumor, therefore the target of reducing "the morbidity and mortality of malignant tumor" can not be effectively achieved by these instruments.

Taking the most widely used endoscope as an example, the endoscope is widely used in diagnosis since it can enter the human body and does not cause great damage. The endoscope is developed and applied for almost half a century, and the technology is very mature and still in the process of development. Magnifying endoscopy, and ultrasonic endoscope have been developed so far, and the latest technology is confocal laser scanning endoscope (CLE). The most advanced confocal microscopy technology and sectional slices technology are used in the confocal laser scanning endoscope (CLE). An image of quasi-cellular level can be obtained (The image is a black-and-white image with unclear gradation, therefore, it can not be deemed as cellular level, but only quasi-cellular level). Confocal laser scanning endoscope (CLE) can improve the imaging level of endoscope to a new standard, and theoretically, it should greatly improve the efficiency of tumor diagnosis, however, it is not the case in actual application. Even with the help of confocal laser scanning endoscope (CLE), doctors still can not detect malignant tumors smaller than 5 mm. The reason is that confocal laser scanning endoscope (CLE) only provides images, and the final judgments are still made by the doctors based on the morphological principle and their own experience. In addition, the imaging area of confocal laser scanning endoscope (CLE) is small when providing a higher-resolution image, due to the imaging capability of confocal laser scanning endoscope (CLE) at quasi-cellular level. This requires doctors to accurately select detecting points, and the selection of detecting points is also empirically made by a doctor based on some images of lower resolution, which, theoretically, is still results from morphological judgment. Therefore, tumors in the stage of precancerous lesion, especially the malignant tumors smaller than 5 mm, cannot be effectively detected only by the method of improving image resolution, since current diagnostic methods mainly remain at the morphological level.

SUMMARY OF INVENTION

The purpose of the present invention is to provide an equipment and method for identifying tumors in the stage of precancerous lesion, especially malignant tumors smaller than 5 mm.

According to one embodiment, the present invention provides an optical observation equipment for identifying the forming process of a malignant tumor, and the optical observation equipment has a receiving space and a transparent front end, which comprises:

a light-guide fiber, the input end of which extends to the receiving space and the output end of which extends to the transparent front end;

a laser emitter, which is disposed in the receiving space and emits laser with a wavelength of 340 nm±20 nm and an energy of 0.3~0.5 mj/m² in a pulsing mode;

a focusing device, which is disposed in the receiving space and coupled to the output end of the laser emitter, and which is used for focusing the laser to the input end of the light-guide fiber;

a white light emitter, which is disposed in the receiving space and emits white light, and the white light is guided into the input end of the light-guide fiber, wherein the laser emitter and the white light emitter are alternately turned on;

a image sensor, which is disposed in the transparent front end, and which is used for acquiring an image of an area irradiated by light emitted from the output end of the light-guide fiber and converting a light signal into an electric signal;

a high-gain amplifier, which is coupled to the image sensor and is used for amplifying the electric signal generated by the image sensor;

and a encoding and emitting device, which is coupled to the high-gain amplifier and is used for encoding the output of the high gain amplifier and emitting the encoded signal.

In one embodiment, the encoded signal emitted by the encoding and emitting device is received and decoded by a receiving and decoding device, and then provided to an image processing device which restores the image acquired by the image sensor and displays the image.

In one embodiment, the laser emitter has a rated output energy >10 mj, a output pulse width <5 ns, a single pulse power >100 KW, and a repeat frequency of 1~50 times/s.

In one embodiment, the white light emitter is one or several LED(s), and the LED is aligned with the input end of the light-guide fiber. The spectrum of LED is solar spectrum with a color temperature of 5000K±400K.

In one embodiment, the light-guide fiber is quartz light-guide fiber or liquid light-guide fiber which is suitable for the transmission of ultraviolet band and visible band.

In one embodiment, the light-guide fiber shows low decay rate within the wavelength range from 300 nm to 700 nm.

In one embodiment, a graphene photosensitive element is used in the image sensor, which can perceive the fluorescence with an intensity of 0.2 lux~0.6 lux.

According to one embodiment, the present invention provides a method for identifying the forming process of a malignant tumor by using the above mentioned optical observation equipment comprising:

aligning the transparent front end of the optical observation equipment with tissue to be detected;

turning off the laser emitter, turning on the white light emitter, and irradiating the tissue to be detected with the white light emitted from the output end of the light-guide fiber;

displaying the image of the tissue to be detected which is irradiated by the white light in a display via the image sensor, the high-gain amplifier, the encoding and emitting device, the receiving and decoding device and the image processing device, and identifying suspected tissue area;

turning off the white light emitter, turning on the laser emitter, and irradiating the suspected tissue area with the laser emitted from the output end of the light-guide fiberin a pulse mode;

displaying the fluorescence image of the suspected tissue area which is irradiated by the laser in the display via the image sensor, the high-gain amplifier, the encoding and emitting device, the receiving and decoding device and the image processing device;

identifying whether or not the suspected area is relevant to malignant tumor on the basis of fluorescence color, wherein the peak value of energy at 460 nm±20 nm of normal tissue is used as a reference, if the peak value at 460 nm±20 nm is 100% of the reference value, there is no other peak values, and the fluorescence color is blue and white, the tissue is identified as normal tissue;

if the peak value at 460 nm±20 nm is more than 60% of the reference value, there is no other peak values, and the fluorescence color is orange or orange red, the tissue is identified as benign lesion tissue;

if the peak value at 460 nm±20 nm is less than 40% of the reference value, and there are peak values at 400 nm±20 nm and 670 nm±20 nm, and the fluorescence color is violet red, the tissue is identified as malignant tumor tissue;

if the peak value at 460 nm±20 nm is less than 40% of the reference value, there is peak value at 400 nm±20 nm, and the fluorescence color is violet, the tissue is identified as severe atypical hyperplasia tissue;

if the peak value at 460 nm±20 nm is less than 40% of the reference value, and there is peak value at 670 nm±20 nm, and the fluorescence color is dark red, the tissue is identified as severe atypical hyperplasia tissue;

and if the peak value at 460 nm±20 nm is less than 40% of the reference value, there is no other peak values, and the fluorescence color is dark color, the tissue is identified as mild or moderate atypical hyperplasia tissue.

According to one embodiment, the present invention provides an endoscope for identifying the forming process of a malignant tumor, and in the front end of endoscope, there is the above mentioned optical observation equipment.

In one embodiment, in the endoscope, there is also a image processing terminal which comprises a receiving and decoding device, an image processing device and a display; the encoded signal emitted by the encoding and emitting device is received and decoded by the receiving and decoding device, and then provided to the image processing device which restores the image acquired by the image sensor and displays the image by the display.

According to one embodiment, the present invention provides a method for identifying the forming process of a malignant tumor by using the above mentioned endoscope, comprising:

stretching the endoscope into a human body, and letting the front end of endoscope reach the position of tissue to be detected;

turning off the laser emitter, turning on the white light emitter, and irradiating the tissue to be detected with the white light emitted from the output end of the light-guide fiber;

displaying the image of the tissue to be detected which is irradiated by the white light in a display via the image sensor, the high-gain amplifier, the encoding and emitting device, the receiving and decoding device and the image processing device, and identifying suspected tissue area;

turning off the white light emitter, turning on the laser emitter, and irradiating the suspected tissue area with the laser emitted from the output end of the light-guide fiber in a pulse mode;

displaying the fluorescence image of the suspected tissue area which is irradiated by the laser in the display via the image sensor, the high-gain amplifier, the encoding and emitting device, the receiving and decoding device and the image processing device;

identifying whether or not the suspected area is relevant to malignant tumor on the basis of fluorescence color, wherein the peak value of energy at 460 nm±20 nm of normal tissue is used as a reference, if the peak value at 460 nm±20 nm is 100% of the reference value, there is no other peak values, and the fluorescence color is blue and white, the tissue is identified as normal tissue;

if the peak value at 460 nm±20 nm is more than 60% of the reference value, there is no other peak values, and the fluorescence color is orange or orange red, the tissue is identified as benign lesion tissue;

if the peak value at 460 nm±20 nm is less than 40% of the reference value, there are peak values at 400 nm±20 nm and 670 nm±20 nm, and the fluorescence color is violet red, the tissue is identified as malignant tumor tissue;

if the peak value at 460 nm±20 nm is less than 40% of the reference value, there is peak value at 400 nm±20 nm, and the fluorescence color is violet, the tissue is identified as severe atypical hyperplasia tissue;

if the peak value at 460 nm±20 nm is less than 40% of the reference value, there is peak value at 670 nm±20 nm, and the fluorescence color is dark red, the tissue is identified as severe atypical hyperplasia tissue;

if the peak value at 460 nm±20 nm is less than 40% of the reference value, there is no other peak values, and the fluorescence color is dark color, the tissue is identified as mild or moderate atypical hyperplasia tissue.

The optical observation equipment, the endoscope using the optical observation equipment and the related identification method of the present invention can identify the tumors the in stage of precancerous lesion, especially the malignant tumors smaller than 5 mm in time.

DESCRIPTION OF DRAWINGS

The above mentioned and other characteristics, properties and advantages of the present invention will become more obvious through the following description in combination with the drawings and examples. The same reference sign in the drawings always represents same features, wherein:

FIG. 2A is a characteristic curve of inherent fluorescence spectrum of normal tissue.

FIG. 2B is a characteristic curve of inherent fluorescence spectrum of benign lesion tissue.

FIG. 2C is a characteristic curve of inherent fluorescence spectrum of cancer tissue.

FIG. 2D is a characteristic curve of inherent fluorescence spectrum of severe atypical hyperplasia tissue.

FIG. 2E is a characteristic curve of inherent fluorescence spectrum of severe atypical hyperplasia tissue.

FIG. 2F is a characteristic curve of inherent fluorescence spectrum of mild or moderate atypical hyperplasia tissue.

EMBODIMENTS FOR CARRYING OUT THE PRESENT INVENTION

Human tumors are generally divided into two categories, i.e., benign tumors and malignant tumors. According to the pathological classification, all of malignant tumors are derived from four kinds of tissues, i.e., epithelial tissue, mesenchymal tissue, lymphoid hematopoietic tissue, and neural tissue. Malignant tumors derived from epithelial tissue are collectively referred to as cancer. Cancer is developed inside epithelial layer. The thickness of epithelium tissue greatly varies in different organs, which is about 0.6 mm to 1.6 mm. However, the common point between them is that the lesions in early stage, which are also called precancerous lesions, occur in the thin epithelial tissue. The precancerous lesions are atypical hyperplasia according to the pathological classification. The atypical hyperplasia can be divided into three levels. The lesions are reserved within the epithelial layer, the scientific name of which is "intraepithelial neoplasia". If this kinds of tumors can be detected timely in the stage of precancerous lesion, there is great promise for curing them. As mentioned above, the stage of precancerous lesion, during which lesions are smaller than 5 mm, is the best period to diagnose and treat malignant tumors. The purpose of the present invention is to dramatically improve the detection rate of malignant tumors in the stage of precancerous lesion.

Figure 1A:
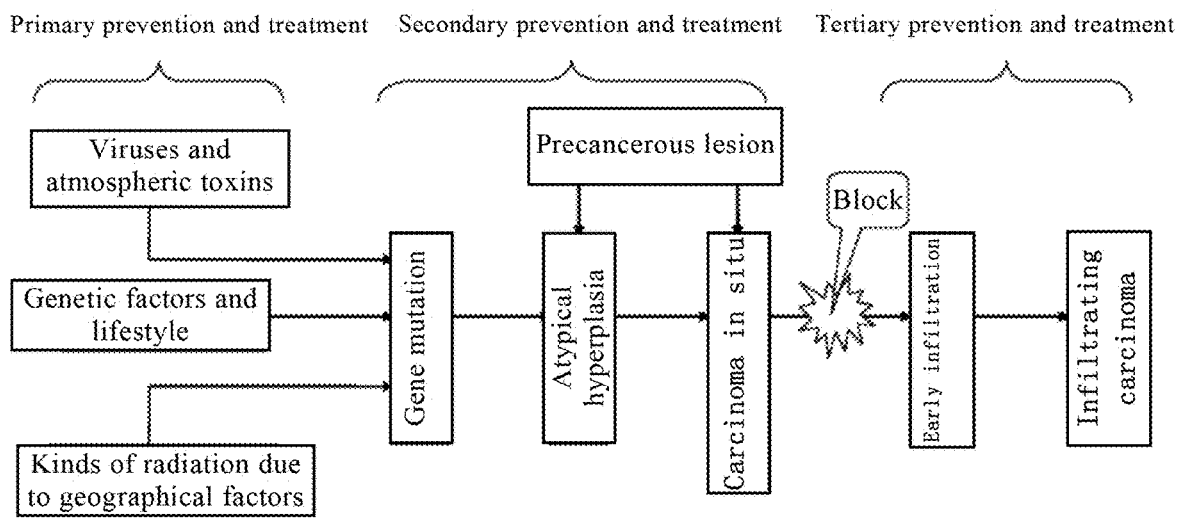
FIG. 1A shows a schematic diagram of the concept about preventing and treating malignant tumor (cancer).

FIG. 1A shows a schematic diagram of the concept about preventing and treating malignant tumor (cancer). As shown in the figure, the prevention and treatment of malignant tumor (cancer) can be divided into three stages, which is also known as prevention and treatment of three levels:

Primary prevention and treatment refers to the prevention mainly aimed at external environment, including cleaning and reducing viruses and atmospheric toxins, modifying lifestyle, investigating genetic factors, and reducing all kinds of radiation due to geographical factors. Such primary prevention and treatment mainly aims at induction factors causing gene mutation. The primary prevention and treatment involves so many factors, and not all of the induction factors will cause gene mutation, so the primary prevention and treatment currently still is a concept.

Secondary prevention and treatment refers to the detection of precancerous lesion stage. As shown in FIG. 1A, there is an atypical hyperplasia stage and a carcinoma in situ stage after gene mutation, and both of the two stages are precancerous lesion stage. "Infiltrating carcinoma" is not yet formed at these stages, and there is an incubation period for up to 5~6 years. These stages are the best time for treating malignant tumor and also the time period to which the identification method of the present invention aims. As shown in FIG. 1A, if timely and effective block can be carried on before carcinoma in situ evolves into early invasion, it will be a perfect time for the prevention and treatment of cancer.

Tertiary prevention and treatment refers to the treatment of "cancer". When entering the period of tertiary prevention and treatment, cancer has emerged which is early infiltrating carcinoma or infiltrating carcinoma. The treatment at this stage is currently used various means. But, in fact, after entering this stage cancer has been in an irreversible state.

85% of human malignant tumors derive from epithelial tissue. Of course, human malignant tumors also derive from mesenchymal tissue, lymphoid hematopoietic tissue, and neural tissue. No matter what kind of tissue a malignant tumor derives from, a long gradual process is necessary for the malignant transformation of cells. This process is known as precancerous lesion or atypical hyperplasia stage, which is also referred to the latency of malignant tumor, and the incubation period of which is usually 5~6 years. Patients in the stage of atypical hyperplasia are not malignant tumor patients in the normal sense. Atypical hyperplasia and carcinoma in situ are pathologically known as abnormal hyperplasia. Because most of lesions of abnormal hyperplasia are heteromorphic cells and a small amount of cancer cells, such abnormal hyperplasia are more likely to malignant transformation. The formation of malignant cells was not an isolated event, which needs special living environment and living condition. Malignant cells are unlikely to generate without a host providing the special environment and condition. In addition, from the perspective of molecular biology, several steps are necessary for the transformation of malignant cells from normal cells. In such process, the biochemistry environment around the cell has substantially changed, such as gene mutation, which leads to abnormal gene expression. While changes of protein and enzyme in cells would inevitably lead to various changes in metabolism, such as metabolism of porphyrin metabolism, including growth factors and hormones generated by host as well as distribution and combination of vascular for the rapid growth of malignant cells. When these prerequisites have been formed, malignant cells have conditions to survive.

Figure 1B:
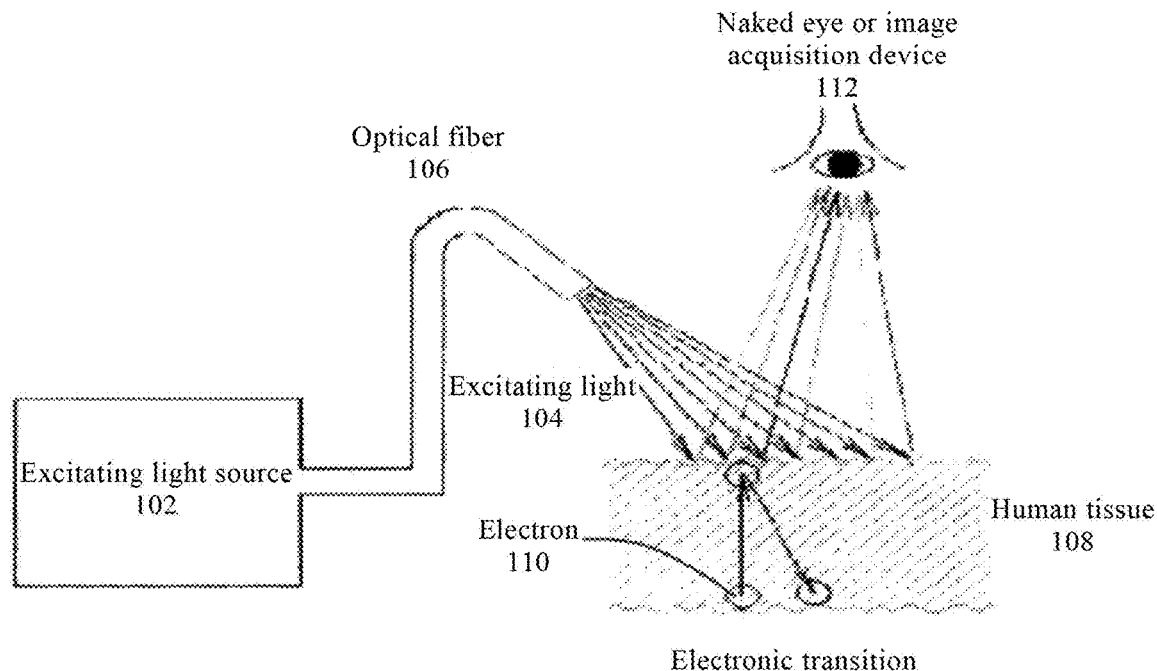
FIG. 1B shows a schematic diagram of detecting human tissue (mainly epithelial tissue or mucosa) with excitation light.

Biology research on the level of electron is quantum biology, which uses quantum mechanics as a tool in the research of biology, i.e., research in sub-molecular biology on the level of electron. Due to the advances in molecular biology and quantum biology, understanding of humans themselves has been greatly improved. The human body is made up of many molecules, mostly of which are protein macromolecules. Of course, all of biological reactions can be regarded as molecular reactions. However, the applicant believes that these reactions should not be merely reactions of macromolecules, but some smaller, more reactive and more sensitive units should participate. These units can only be non-localized electrons with high reactivity. Such single electron is prone to be motivated and strongly absorb photons, thereby exhibiting a strong color. A molecule with such unpaired electron is known as free radical, which is highly reactive (also known as electronic non-locality), therefore such molecule may produce rapid interaction with important biological significance. Except the $\pi$ electron of a conjugated double bond has mobility, there are many possibilities for generation of non-locality of electrons. The color shown by fluorescence in visible light band also results from the interaction between electrons and photons. When a photon enters a substance, two cases may occur: one is that the energy is hardly absorbed after entering the substance, another is that all or part of the energy is absorbed. In the latter case, the energy of the light is transferred to molecule during the absorption process. However, the absorption itself is a highly specific phenomenon, that is, a molecular with a certain structure can only absorb a light radiation with a certain energy. As long as the energy of excitation light is strong enough, the excited molecule can obtain higher energy and transition to higher energy state. Then the molecule will transfer part of the energy to surrounding molecules through internal conversion process and return to the lowest excited state. If it does not consume energy through internal conversion and return to ground state, but releases energy by emitting corresponding photons, that is fluorescence emission. The molecular structure and surrounding environment of various species (including the biochemical environment of malignant tumor) are different. They all exhibit their own particular spectral frequency when a light of particular frequency irradiating the material (including human tissues). FIG. 1B shows a schematic diagram of detecting human tissue (mainly epithelial tissue or mucosa) with excitation light source. Wherein, an excitation light 104 emitted by a excitation light source 102 irradiate human tissue 108 (mainly epithelial tissue or mucosa) through an optical fiber 106. Electronic transition is occurred within the human tissue 108. Fluorescence is produced during the transition process of electron 110 and acquired by naked eyes or an image acquisition device 112. It can be known according to the above fluorescence mechanism, the generation of fluorescence is resulted from the change of quantum states within the molecular structure. Different molecular structures can produce different fluorescence wavelengths. At present, the basic biochemical environment surrounding a malignant tumor remains unknown, however, if there is an external exciting light with enough energy to excite malignant tumor and normal tissue, the malignant tumor and normal tissue will absorb corresponding photons which can be absorbed by them, respectively, and then return to the ground state by releasing the energy of the absorbed photons in the form of fluorescence. This released fluorescence spectrum contains a great deal of surrounding biochemical information of malignant tumor and normal tissue. The diagnostic criteria for identifying the fluorescence spectrum and fluorescence image of malignant tumor, atypical hyperplasia and benign lesion can be established with the aid of the acquired fluorescence information.

The distribution of fluorescence spectrum directly reflects the change in the energy distribution of different excited states inside a molecular structure. The optical properties of the molecule are determined by the electronic structure in a molecular, which represent the basic independent structure of each molecule. The inherent fluorescence spectrum can display characteristics of one molecular. Similarly, when a human tissue is detected using the inherent fluorescence spectrum technology, the molecular characteristics of the human tissue can also be definitely displayed. If the detected human tissue is malignant tumor tissue, atypical hyperplasia tissue, inflammatory, ulcers or normal tissue, the characteristic curve of inherent fluorescence spectrum and color image of inherent fluorescence spectrum corresponding to their own characteristics will be displayed.

The present disclosure selects macromolecular clusters—NADH reduced nicotinamide adenine dinucleotide, porphyrins, and structural proteins (collagen, elastin) that are related to cancer formation in epithelial tissues and are excited to emit intrinsic fluorescence as the material basis for tracking and studying that the normal cells in epithelial tissues gradually disintegrate into inflammatory cells, atypical cells, and cancer cells. The above-mentioned three macromolecular clusters have the following commonalities: firstly, they are closely related to cell disintegration; secondly, they all emit fluorescence after being excited by excitation light; thirdly, the fluorescence spectra generated are all in the visible light band of 400 nm-700 nm (which is conducive to the doctors' visual identification).

(1) The Theoretical Basis of NADH as an Indicator

Figure 5:
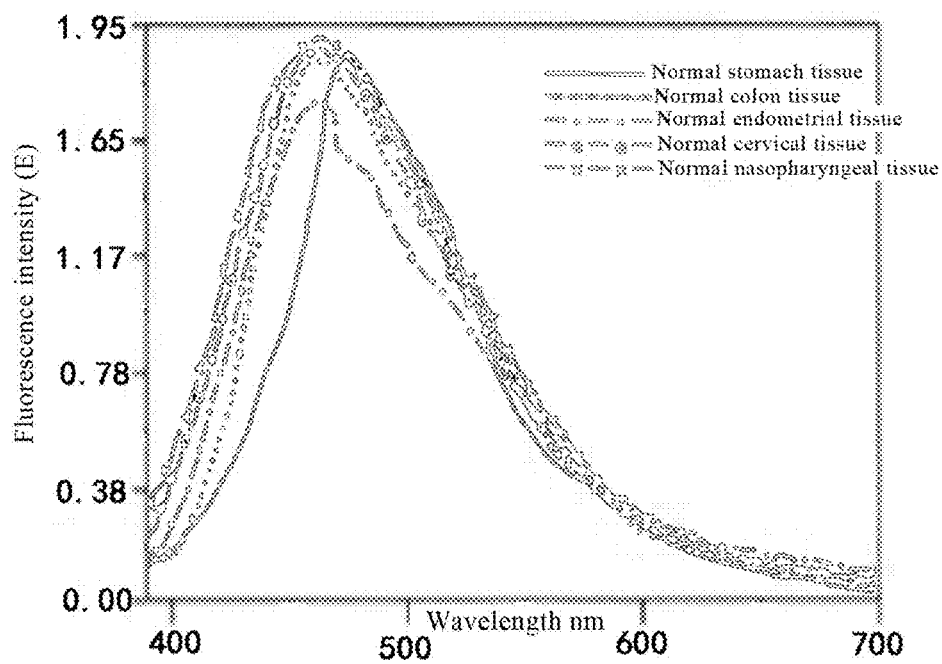
FIG. 5 shows NADH fluorescence spectrum curves of normal human epithelial tissues according to one embodiment of the present invention.

Reduced nicotinamide adenine dinucleotide (NADH) and its oxidized form (NAD+) are the most important coenzymes in the human body. They can use external fat and protein as energy to provide the high-energy phosphate compound ATP required by human cells, and can be widely involved in the material, energy metabolism, signal transduction and gene regulation in normal human cells, and are directly related to cell metastasis. The original source of electrons in the respiratory chain is NADH. NADH is produced by normal cells during alienation (catabolism). To a certain extent, the conversion rate of NADH/NAD+ represents the metabolic activity of normal cells. Therefore, the intrinsic fluorescence analysis method is used to analyze the content of NADH in cells to evaluate the metabolic activity of normal cells. FIG. 5 shows the measured inherent fluorescence spectrum curves of NADH of normal epithelial tissues in different parts of the human body, which comprise normal gastric epithelial tissue, normal colon epithelial tissue, normal endometrial epithelial tissue, normal cervical epithelial tissue, and normal nasopharyngeal epithelial tissue. After the normal human epithelial tissues are excited by excitation light with a wavelength of 337 nm, NADH inherent fluorescence spectrum curves of the tissues are obtained. From the inherent fluorescence spectrum curves in FIG. 5, it can be seen that normal human epithelial tissue can produce a strong NADH fluorescence spectrum curve with a peak wavelength of 470 nm after being excited by the excitation light with a wavelength of 337 nm, that is, the relative value of NADH contained in normal human epithelial tissue is measured. It can be seen that the NADH fluorescence peak difference of various normal human epithelial tissues is not more than 10 nm.

In the 1920s, German physiologist Otto Warburg discovered the difference in energy metabolism between cancer cells and normal cells. The only source of energy for cancer cells is sugar, while the main source of energy for normal cells is fat and protein. Dr. Seyfried released research results on the formation of cancer in 2012. He deems that the initial source of cancer is caused by damage to the mitochondria in the cell. Mitochondria are an organelle in the cell. They are the energy processing plant of the cell. With the participation of aerobic, through a series of biochemical reactions, mitochondria convert glucose into energy. It is obvious that this is a biochemical reaction with the participation of aerobic. Therefore, NADH provides sufficient energy to normal cells with the respiratory chain in normal cells participates. That is to say, the energy provided by normal cells depends on NADH provided under aerobic conditions. If too many mitochondria in the cells are destroyed, the cells cannot generate enough energy through NADH aerobic participation to meet the needs of the cells. The destruction of mitochondria in cells is the initial phenomenon of cell canceration, and it also shows the main reason for the decrease of NADH content in atypical cells. At this time, in order for atypical cells to survive, they must obtain energy from other approaches that do not require the participation of mitochondria and NADH. This approach is anaerobic metabolism, that is, sugar fermentation. However, normal cells do not have the function of sugar fermentation. Therefore, the detection of NADH content in human epithelial tissue is one of the theoretical basis for identifying whether the tested epithelial tissue has become cancerous or not.

Figure 6:
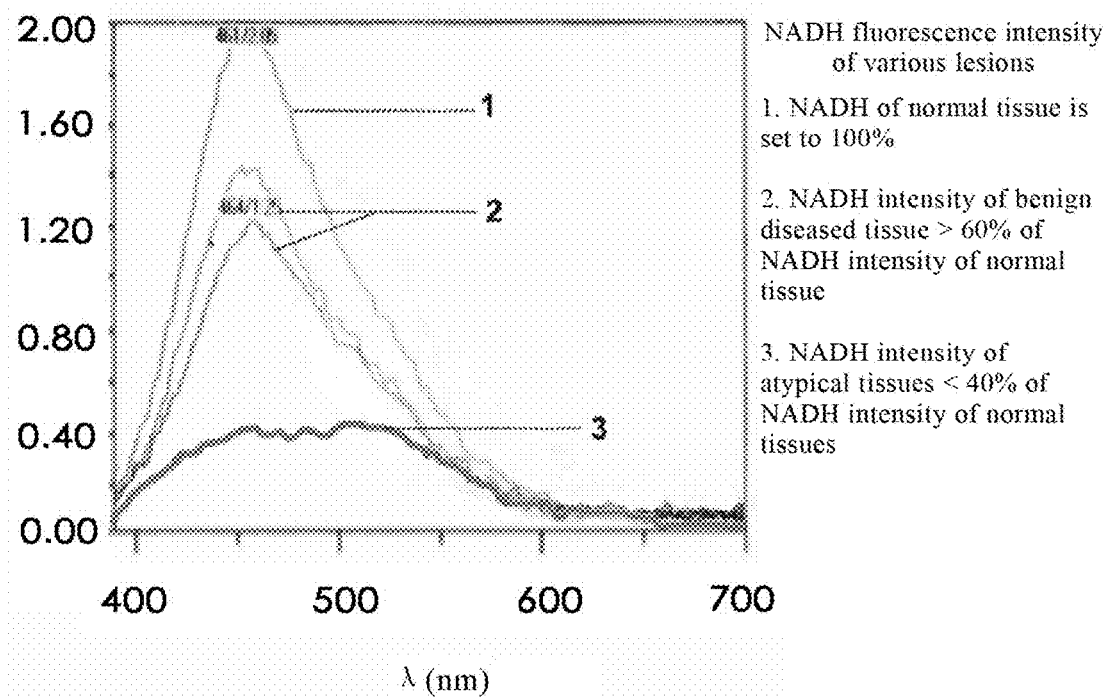
FIG. 6 shows NADH fluorescence intensity of various lesions according to one embodiment of the present invention.

When we apply fluorescence detection in clinical cases, we first move the fluorescence detection probe to the normal epithelial tissue away from the lesion to detect the NADH fluorescence intensity of the normal tissue, and the measured NADH fluorescence intensity of the normal tissue is set to 100%. Then the suspicious lesion tissue is detected with the probe. The measured NADH fluorescence intensity of the suspicious lesion is shown in FIG. 6. FIG. 6 shows the statistical data of the relative content of NADH in various human epithelial tissues (including normal epithelial tissue, epithelial tissue with benign lesions, atypical hyperplastic epithelial tissue, and cancerous epithelial tissue) obtained through the detection of millions of cases. From the analysis of the relative amount of NADH contained in the above-mentioned various types of epithelial tissues, we found that there are corresponding regulations for the relative content of NADH in various types of epithelial tissues.

Firstly: NADH content is highest in normal epithelial tissue. The fluorescent color is blue.

Secondly: NADH content in epithelial tissue with benign lesions is 60% of NADH content in normal tissue. The fluorescent color is orange.

Thirdly: NADH content in atypical growing epithelial tissues is only about 40% of the NADH content in normal epithelial tissues. The fluorescent color is dark.

Because of the characteristics of rapid growth of cancer tissue and the abnormal vascular structure of tumor tissue, the blood supply is reduced. Therefore, hypoxia is a state in which cancer cells are ubiquitous. The microenvironment stimulates the transcription of hypoxia inducible factor HIF. The activation of HIF increases the expression of glucose transport to sugar fermentation and accelerates sugar fermentation. As a result, the production of lactic acid increases and oxygen is saved under hypoxic conditions. Cancer cells have unique characteristics of energy metabolism. The growth and proliferation of hypoxic cancer cells requires stable energy to maintain metabolism. Sugar intake is their biological characteristic. Changes in the metabolism of cancer cells cause changes in metabolites and enzymes, weakened the catabolism of amino acid, loss of certain enzyme components and impaired synthesis, decreased concentrations of enzymes (NADH or NADPH) and FAD in cancer tissues, and most likely to cause a decrease in the fluorescence energy of NADH in cancer tissues.

The NADH content in cancer epithelial tissue and atypical cell epithelial tissue is significantly lower than that in normal cell epithelial tissue. There are various explanations for its mechanism, and the common point is the difference in energy metabolism of cancer epithelial tissue. This discovery of natural laws in the human body has laid a scientific basis for the identification and diagnosis of cancer cell epithelial tissue, atypical cell epithelial tissue, benign cell epithelial tissue, and normal cell epithelial tissue.

(2) The Theoretical Basis of Porphyrin as an Indicator

Porphyrin is one of the important substances in the life activities of the human body, and it is closely related to certain physiological functions in the body. Therefore, porphyrins are related to dysplasia and certain diseases of the body. The porphyrins bound to iron and protein are carriers of oxygen and also have active enzymes. Therefore, the metabolism of porphyrins is related to certain diseases of the body. In 1949, Figge et al. reported that porphyrin has a high affinity for cancer and will be retained in the epithelium of cancer tissue, but its content in the epithelium of cancer tissue and normal epithelium is affected by many factors, such as pH, wherein the pH value of cancer tissue is relatively small, therefore, porphyrin can enter the epithelium of cancer tissue more and complete the preferential aggregation in cancer tissue. The aggregation mechanism of porphyrin in cancer tissue is still inconclusive, but the phenomenon that porphyrin can be retained in cancer tissue epithelium has been confirmed by scientists. However, the content of porphyrin in normal human epithelial tissue is extremely low, and the porphyrin content of the epithelial tissue in the active state of the human body cannot be detected by conventional detection methods. For routine detection of porphyrin content in human epithelial tissue, an in vitro method is used, that is, a sample of human epithelial tissue is grabbed from the human body, and the tissue fluid is obtained after crushing and centrifugation, and then the trace porphyrin data of the sample can be detected by fluorescence spectrometer. To detect the porphyrin content in the epithelial tissue under the condition of human carrier (such as endoscopy, during surgery), it is impossible to obtain the presence of porphyrin content using conventional methods. We found that the sensitized fluorescence method can only measure porphyrin data through a special detection method.

(3) The Discovery of Sensitized Fluorescence Realizes the Possibility of Detecting Porphyrin in Human Body When a nitrogen molecular pulsed laser is used to excite light with a wavelength of 337 nm, the absorption peak of porphyrin is 384 nm, and the fluorescence spectrum of porphyrin has two peaks at 630 nm and 690 nm. Both the detection method and the porphyrin specimens were measured by a conventional fluorescence spectrometer in the laboratory. However, due to the low content of porphyrin in human epithelial tissue, we adopted a sensitized fluorescence detection method, which effectively solved the method of detecting trace porphyrin in epithelial tissue in human body. Sensitized fluorescence detection method: when the fluorescence intensity of certain substances is too low, it cannot be detected by general fluorescence detection methods. Then we find certain substances, through the process of energy transfer, the excitation energy is transferred to the energy acceptor, so that the energy acceptor molecule is excited again, and the intensity of the fluorescence emitted by the acceptor can be enhanced.

We choose elastin and collagen, which are widely present in human epithelial tissue, and can be used as a donor for energy transfer. When the excitation light is 337 nm, the fluorescence peak of human elastin is 400 nm.

The fluorescence peak of elastin is used as the donor, and the fluorescence spectrum of the acceptor porphyrin under the excitation of light with a wavelength of 337 nm has a strong and broad absorption bandwidth around 384 nm. Steinberg et al. believe that the core of sensitized fluorescence is that the donor must have a fluorescence spectrum, and the acceptor must have a strong absorption bandwidth. The fluorescence spectrum of the donor must be overlapped with the absorption spectrum of the acceptor. However, the spectrums of the two must not exceed a certain level distance. For example, the peak of the fluorescence spectrum of the donor elastin is 400 nm, and the absorption peak of the acceptor porphyrin is 384 nm, and the gap between the donor and the acceptor is 16 nm. This gap meets the energy transfer conditions.

That is, after the donor elastic protein is excited by the excitation light at 337 nm, the excited molecule carries the energy to transition to a high energy level, and then releasing the excess energy when it falls from the high energy level to the low energy level (that is, the generation of fluorescence). The excess energy is absorbed by the peak of the absorption spectrum of elastin at 384 nm, so that the porphyrin receives two excitations, thus the fluorescence peak of the porphyrin is greatly increased. The fluorescence intensity of porphyrin is greatly increased after porphyrin is excited twice. The application of sensitized fluorescence detection method solves the problem that it is difficult to detect the porphyrin content in the epithelial tissue of the human body (in the carrier state). During this energy transfer process, because part of the energy of elastin is transferred to the absorption peak of porphyrin, the fluorescence value of elastin decreases in energy, from the original 400 nm redshift to about 420 nm. The appearance of the characteristic fluorescence peak at 420 nm also confirms the basis for the inclusion of porphyrin in the measured human epithelial tissue.

From the discovery of sensitized fluorescence, it is possible to detect porphyrin fluorescence at 630 nm, 690 nm (red color) and 420 nm (violet color) in the human body. Therefore, violet fluorescence, violet red fluorescence and dark red fluorescence will appear in clinical diagnosis.

(4) Theoretical Basis Applied to the Identification Criteria of Lighting Lesions The theoretical basis for the above-mentioned intrinsic fluorescence to light various types of epithelial lesions is that the use of near-ultraviolet excitation light to excite the fluorescent molecular clusters related to abnormal cells in the epithelial tissue, namely NADH, porphyrin, and protein sensitization fluorescence. Use multiple parameters measured to identify epithelial tissue lesions, rather than using a single parameter to identify epithelial tissue lesions. Using the measured multi-parameter data through the calculation of their ratio values, the measured tissue can be distinguished as normal epithelial tissue, epithelial tissue with benign lesions, atypical proliferating epithelial tissue or cancerous epithelial tissue.

NADH reduced nicotinamide adenine dinucleotide is a necessary coenzyme for all normal cell energy metabolism. The peak intensity of NADH fluorescence measured in epithelial tissue is proportional to the level of NADH in the cell. The higher the level of NADH in the cell, the higher the aerobic energy metabolism in the cell. Conversely, after atypical cells and cancer cells are damaged due to intracellular mitochondria, aerobic energy metabolism gradually decreases, and at the same time the intracellular NADH level in the cell also gradually decreases. Therefore, monitoring the NADH level in the epithelial tissue can monitor the path of the occurrence and development that the normal cells in the epithelial tissue-→abnormal cells-→cancer cells. If only the NADH trace data is used to identify the whole process of evolving from normal cells to cancer cells, it is flawed and incomplete, because it can only prove the transformation of aerobic energy metabolism in cells to anaerobic metabolism, that is, the process of transition from normal cells to heterogeneous cells, but it cannot distinguish the difference between atypical cells and cancer cells. Because the NADH theoretical analysis can only prove the abnormality of cell energy metabolism, but cannot verify that the tissue has all met the specific indicators of cancers.

The participation of porphyrin and protein-sensitized fluorescence can completely identify and distinguish the whole process of human epithelial tissue from normal j cells ——→ cells with benign lesions ——→ heterogeneous cells ——→ cancer cells.

(5) Fluorescent Color Image Identification Standard

The core content of intrinsic fluorescence lighting up epithelial tissue lesions is to provide an intrinsic fluorescence image that can display various types of epithelial lesions in different colors. The doctors can qualitatively distinguish whether the tested epithelial tissue is normal epithelial tissue, epithelial tissue with benign lesions, atypical growth epithelial tissue, or cancer epithelial tissue by visual detection. Intrinsic fluorescence lights up the macromolecular porphyrin, NADH, and protein that are closely related to cancer and can emit fluorescence. The fluorescence spectra emitted by them are all implemented in the range of visible light 400 nm-700 nm. Therefore, doctors can visually identify and qualitative various types of epithelial tissue lesions. Because the fluorescence spectra of various types of lesions in epithelial tissues are implemented in the visible light band. The visible light band contains seven colors: red, orange, yellow, green, blue, indigo, and purple. Therefore, there is a corresponding relationship between the fluorescence spectrum curve and the color distribution in the visible light band. The intensity of the peak of the fluorescence spectrum curve also represents the intensity of the color block (color unit) of the corresponding segment. The higher the peak value, the larger the proportion of the color block corresponding to the peak, and the stronger the color rendering ability. On the contrary, the lower the peak value, the smaller the proportion of the color patch corresponding to the peak, and the weaker the color rendering ability. The color blocks in the range of 400 nm-700 nm are superimposed according to the fluorescence spectrum curve to form a fluorescence chromatogram. Therefore, the connotation of the intrinsic fluorescence spectrum curve of various lesions is the intrinsic fluorescence chromatographic energy distribution map. As we all know, the three primary colors of color are red, green and blue, that is, the seven colors of red, orange, yellow, green, blue, indigo, and purple in visible light can be derived from the different ratios of the three colors of red, green and blue. Therefore, the present disclosure defines the color characteristics presented by the fluorescence chromatogram through different ratios of the three colors of red, green and blue.

FIGS. 2A 2F reveal the characteristic curves of inherent fluorescence spectrum and color images of inherent fluorescence spectrum of different human tissues.

FIG. 2A is a fluorescence chromatographic energy distribution diagram of normal epithelial tissue in human, which is a single fluorescence chromatographic energy distribution diagram of NADH, with a peak of 470 nm±20 nm (corresponding to blue color) as the main peak. Since its color spectrum contains orange and yellow light (visible light color segments) energy, the characteristic fluorescent color of normal epithelial tissue is off-blue. The corresponding ratio of the three colors (red, green, and blue) is (75%-85%, 95%-100%, 95%-100%), preferably (85%, 100%, 100%).

FIG. 2B is a fluorescence chromatographic energy distribution diagram of epithelial tissue with benign lesions in human, which is a single fluorescence chromatographic energy distribution diagram of NADH, with a peak of 470 nm±20 nm as the main peak. The main peak is only 60% the peak of normal epithelial tissue. As the blue energy corresponding to the main peak decreases, while red, orange, and yellow energy increases, the characteristic fluorescent colors of benign lesions of epithelial tissue are orange or orange red. The corresponding ratio of the three colors (red, green, and blue) is (795%-100%, 55%-65%, 15%-25%), preferably (100%, 60%, 20%).

FIG. 2C is a fluorescence chromatographic energy distribution diagram of cancer epithelial tissue in human. The peak value of NADH fluorescence dropped significantly, and it was less than 40% of the NADH peak value of normal epithelial tissue. Therefore, its characteristic color (blue color) also decreased significantly. The characteristic peak of porphyrin fluorescence at 680 nm±20 nm clearly showed and its corresponding color is red. The characteristic peak of sensitized fluorescence at 420 nm±20 nm clearly showed and its characteristic color is purple. Therefore, the characteristic fluorescent color of human cancer epithelial tissue is violet red. The corresponding ratio of the three colors (red, green, and blue) is (75%-85%, 0%-5%, 55%-65%), preferably, (80%, 0%, 60%).

FIG. 2D is the fluorescence chromatographic energy distribution diagram of severely atypical growth epithelial tissue in human. The peak value of NADH fluorescence dropped significantly, and it was less than 40% of the NADH peak value of normal epithelial tissue. Therefore, its characteristic color (blue color) also decreased significantly. The characteristic peak of porphyrin fluorescence at 680 nm±20 nm clearly showed and its corresponding color is red. The sensitized fluorescence characteristic peak at 420 nm±20 nm did not appear. Therefore, the characteristic fluorescent color of human severely atypical growth epithelial tissue is dark red. The corresponding ratio of the three colors (red, green, and blue) is (40%-50%, 0%-5%, 0%-5%), preferably, (45%, 0%, 0%).

FIG. 2E is the fluorescence chromatographic energy distribution diagram of severely atypical growth epithelial tissue in human. The peak value of NADH fluorescence dropped significantly, and it was less than 40% of the NADH peak value of normal epithelial tissue. Therefore, its characteristic color (blue color) also decreased significantly. The characteristic peak of sensitized fluorescence at 420 nm±20 nm clearly showed and its characteristic fluorescence color is purple. The fluorescence characteristic peak of porphyrin does not appear, so the characteristic fluorescence color of human severely atypical growth epithelial tissue is violet. The corresponding ratio of the three colors (red, green, and blue) is (35%-45%, 0%-5%, 35%-45%), preferably, (40%, 0%, 40%).

FIG. 2F is the fluorescence chromatographic energy distribution of epithelial tissue with mild to moderate atypical growth in human. The peak value of NADH fluorescence dropped significantly, and it was less than 40% of the NADH peak value of normal epithelial tissue. Therefore, its characteristic color (blue color) also decreased significantly. The fluorescence characteristic peak of porphyrin does not appear. The characteristic peak of sensitized fluorescence also does not appear. Therefore, the comprehensive characteristic fluorescent color of the epithelial tissue of light and moderate atypical hyperplasia in the human is dark color. The corresponding ratio of the three colors (red, green, and blue) is (35%-45%, 35%-45%, 15%-25%), preferably, (40%, 40%, 20%).

These curves of inherent fluorescence spectrum and color images of inherent fluorescence truly reflect the biochemistry environment surrounding human tissues. In human tissue, known biological molecules, fluorescence spectrum of which can be detected, comprise amino acid ossein, structure protease and coenzyme, fat and coenzyme related to the cellular metabolic of porphyrin, adenine dinucleotide, flavin adenine dinucleotide (NADH) and flavin mononucleotide, tryptophan, collagen, adermin, elastin, fat intestinal pigment, acriflavine, porphyrin and so on. These molecules will emit respective inherent fluorescence spectrum after being excited by special light, thereby exhibiting their characteristics.

More than 1000 cases of ex vivo specimens removed by surgery have been studied, including specimens of gastric cancer, gastric ulcer, colon adenocarcinoma, endometrial carcinoma. The preferred excitation wavelength and the function relationship of energy and emitted light (EEMexcitation-emission matnrices) are studied, i.e., the most effective excitation wavelength and energy conforming to human tissue for exciting the inherent fluorescence are explored. According to the theoretical analysis, longer wavelength and lower energy should be selected to ensure sufficient strength of effective intrinsic fluorescence of human tissue, since short wavelength and high energy are prone to damage the living human tissue and make it photolysis, i.e., "bleached". The requirement on the energy of excitation light reaching tissue is based on real-time detection of thickness of epithelial tissue, and is determined as not more than 0.3~0.5 mj/m$^2$. Through extensive testing and analysis, the following conclusions are obtained:

1) Wavelength of Exciting Light

The light-emitting properties of exciting light on the complex of protoporphyrin (protoprphynins Ix bisodium, PP) and bovine serum albumin (Bovinsserdium albu-min, BSA) were studied in a tube. Wavelengths of exciting light were selected as follows: 337 nm, 365 nm, 405 nm. Upon analysis, it is found that the intrinsic fluorescence spectra generated by exciting lights at 337 nm, 365 nm on human tissues are similar, and the peak value of 420 nm is obviously missed in the intrinsic fluorescence spectrum curve generated by exciting light at 405 nm. In Table 1, the fluorescence spectral properties of PP, PP-BSA and tumor tissues under different wavelengths of exciting light are shown.

TABLE 1

| Subject | wavelengths of exciting light λ, (nm) | Peak value of fluorescence spectrum |
| --- | --- | --- |
| PP | 337 | 617, 675 |
| PP-BSA | 337 | 422, 635, 675 |
| Cancer tissue | 337 | 420, 640, 680 |
| PP | 365 | 613, 682 |
| PP-BSA | 365 | 430, 635, 690 |
| Cancer tissue | 365 | 640, 690 |
| PP | 405 | 624, 680 |
| PP-BSA | 405 | 630, 680 |
| Cancer tissue | 405 | 630, 690 |

For the fluorescence spectral properties, the more the positions of characteristics peak value, the more accurate the testing result. 337 nm and 365 nm are much better than 405 nm according to the number of positions of peak values. Therefore, the optimal wavelength of exciting light used in human tissue to excite inherent fluorescence is 340 nm±20 nm.

2) Working Mode of Exciting Light

Pulse mode is better than continuous light. For example, the nitrogen molecule laser belongs to exciting light of pulse mode. Its average power is not high, however its pulse power is very high, which is helpful for the exciting light to enter the inner layer of epithelial tissue through the outer layer of epithelial tissue and explore the biochemical changes in the inner layer of epithelial tissue. In an experiment, it was demonstrated that the exciting light of pulse mode can enter the inner layer of epithelial tissue and discover the characteristic information at 3 mm under the surface of normal mucosa. However, continuous light can not penetrate the epithelial tissue, and the efficient energy of continuous light stays in the outer layer of epithelial tissue, therefore only the inherent fluorescence information of outer layer of epithelial tissue can be detected. Therefore its detectability is not as good as exciting light of pulse mode.

3) Emission Intensity of Exciting Light

The emission intensity of exciting light have basically been determined within a certain range after the wavelength of exciting light was determined at 340 nm±20 nm and the requirement on energy reaching tissue was not higher than 0.3 0.5 mj/m$^2$. The human epithelial tissue varies between individuals, but the overall scope of the emission intensity of exciting light is 0.2 Lux 0.6 Lux. In terms of visual inspection, this intensity belongs to lower intensity, which may cause some difficulties in detection. Therefore, the present invention makes a certain design in dealing with the exciting light of weaker intensity, which will be described in detail later.

4) Basic Principles of Identifying Malignant Tumor, Benign Lesion, Atypical Hyperplasia and Normal Tissue According to the Method of Inherent Fluorescence Image:

The diagnosis principle of inherent fluorescence image method is derived from inherent fluorescence spectrum method. The spectrum method can record all the detailed fluorescence informations of the tested tissues, so curves of inherent fluorescence spectrum from more than ten thousand cases of different human tissues (including oral cavity, esophagus, stomach, duodenum, colon, anus and rectum, cervix, uterus, vagina, vulva, nasopharynx, bronchus, skin, and so on) are detected during the period of experiment and data collection, which includes normal tissue, benign lesion, malignant tumor and atypical hyperplasia. According to verification by pathological section and pathological section reports, diagnosis criteria of inherent fluorescence spectrum method were continuously revised, and following diagnosis principles were ultimately determined:

combining the above mentioned characteristic curves of inherent fluorescence spectrum showed in FIG. 2A to FIG. 2F, among the characteristic curves of inherent fluorescence spectrum of various tissues, the following positions of three wavelengths can be used as characteristic point for identifying:

a) 460 nm±20 nm, the above peak value will inevitably appear in all of the tested tissues, and the peak value at this position of wavelength is used as differential diagnosis;

b) 400 nm±20 nm, different tested tissues behave differently, some have this peak value while some not, and the peak value at this position of wavelength is used as differential diagnosis;

c) 670 nm±20 nm, different tested tissues behave differently, some have this peak value while some not, and the peak value at this position of wavelength is used as differential diagnosis.

Self-comparison method was used when making detection and diagnosis. Firstly, the site of normal tissue, i.e., the normal tissue far away from the site suspected as lesion was detected. First of all, the tissue was irradiated with the exciting light at above wavelength and intensity, and the peak values appeared at 460 nm±20 nm in the characteristic curve of detected inherent fluorescence spectrum were determined as 100%. From the comparison of above FIG. 2A to FIG. 2F, it can be seen that there is only a peak value at 460 nm±20 nm for normal tissue. And for other various of lesions (including benign lesions and malignant lesions at each stage), there were several peak values and the peak values at 460 nm±20 nm decrease significantly.

Then the suspicious tissue was detected:

if in the spectrum curve, the peak value at 460 nm±20 nm is less than 50% of that in normal tissue, it is malignant tumor tissue (possibly in different lesion stages), and if more than 50%, it is benign lesion tissue (FIG. 2B);

if in the spectrum curve, there is a peak value at 400 nm±20 nm, the tissue is identified as malignant tumor tissue or atypical hyperplasia tissue;

if in the spectrum curve, there is a peak value at 670 nm±20 nm, the tissue is identified as malignant tumor tissue or atypical hyperplasia tissue too.

The fluorescence spectrum band of inherent fluorescence spectrum method was designed and recorded at 400 nm~700 nm, and the whole band is visible band. The biochemical reaction of epithelial tissue generated by excitation of exciting light at wavelength of 340 nm+20 nm on epithelial tissue can be recorded. The molecular structure can be explored by the characteristic curve of this inherent fluorescence spectrum. Of course, the curve profile of inherent fluorescence spectrum can also be regarded as energy profile of inherent fluorescence chromatographic energy diagram. Since the whole spectrum band of 400 nm~700 nm is distributed in visible band, the intensity of peak also represents the intensity of color. The peak values of different wavelengths can exhibit different colors since the inherent fluorescence imaging method is implemented in visible band. Doctors can directly identify the nature of lesion according to the fluorescent color of lesion through visual method. Referring to FIG. 2A~ FIG. 2F again.

As shown in FIG. 2A, the property of energy of inherent fluorescence spectrum of normal epithelial tissue is that: there is a main peak with strong energy at 470 nm (blue) and sub-peaks at 500 nm~600 nm (yellow, orange) and 400 nm~450 nm (blue, purple). The whole visual color is "blue and white".

As shown in FIG. 2B, the property of energy of inherent fluorescence spectrum of benign lesion is that: there is a main peak at 470 nm (blue), which is less than the peak value of normal epithelial tissue at 470 nm, and obvious sub-peaks at 480 nm~580 nm. The whole visual color is "orange or orange red".

As shown in FIG. 2C, the property of energy of inherent fluorescence spectrum of malignant tumor tissue is that: there is a main peak at 470 nm (blue) with greatly reduced energy, some energy i at 500 nm~700 nm and there are sub-peaks at 680 nm (red) and 420 nm. The whole visual color is "violet red".

As shown in FIG. 2D, the property of energy of inherent fluorescence spectrum of severe atypical hyperplasia-malignant tumor lesion is that: there is a main peak at 470 nm (blue) with greatly reduced energy, some energy is still retained at 500 nm~700 nm, and there are sub-peaks at 680 nm (red), but there is no sub-peak at 420 nm. The whole visual color is "dark red".

As shown in FIG. 2E, it is also severe atypical hyperplasia-malignant tumor lesion, which is in different stages of progress comparing with the severe atypical hyperplasia-malignant tumor lesion showed in FIG. 2D. And the property of energy of inherent fluorescence spectrum is that: there is a main peak at 470 nm (blue) with greatly reduced energy, some energy is still retained at 500 nm~700 nm, and there are sub-peaks at 420 nm, but there is no sub-peak at 680 nm (red). The whole visual color is "violet".

As shown in FIG. 2F, the property of energy of inherent fluorescence spectrum of mild or moderate atypical hyperplasia lesion is that: there is a main peak at 470 nm (blue) with greatly reduced energy, and there is no sub-peak at 680 nm (red) and 420 nm. The whole visual color is "dark color".

Based on the above mentioned spectrums, the more precise diagnostic criteria of inherent fluorescence spectrum are showed in Table 2: wherein the energy of peak values near three wavelengths: 460 nm±20 nm, 400 nm±20 nm, 670 nm±20 nm are used as main reference.

TABLE 2

| | Energy at 460 nm ± 20 nm | Energy at 400 nm ± 20 nm | Energy at 670 nm ± 20 nm | fluorescent color of detected tissue |
|---|---|---|---|---|
| Normal tissue | 100% | No | No | blue and white |
| benign lesion tissue | >60% | No | No | orange or orange red |
| malignant tumor tttissue | <40% | Yes | Yes | violet red |
| severe atypical hyperplasia->cancer | <40% | Yes | None | violet |
| severe atypical hyperplasia->cancer | <40% | No | Yes | dark red |
| mild or moderate atypical hyperplasia | <40% | No | No | dark color |

Any above lesions are inevitably derived within epithelium, that is, any above lesions are inevitably parasitic in normal epithelial tissue. There is a main peak of strong energy at 470 nm of the fluorescence inherent spectrum of normal epithelial tissue, and its visual color is bright "blue and white". However, the peak value at 470 nm in the inherent fluorescence spectrum of any above lesions, no matter benign lesion, malignant tumor or atypical hyperplasia, is significantly weakened. Therefore, its visual intensity is much less than "blue and white", at least less than 50%~70%. Exciting light sweeps each tissues when taking a quick examination. Each lesion in epithelial tissue will be very obvious against the blue and white background of normal tissues, since the contrast between orange or orange red, violet red, dark red, violet, or dark color and "blue and white" is very significant, and doctors are very easy to visually detect lesion areas. If only a lesion area is to be detected without accurately determining what the lesion is, the presence of a lesion can be preliminarily determined directly according to the color without using self-comparison method.

Optical Observation Equipment

As mentioned above, it is required that the energy reaching tissues is not higher than 0.3~0.5 mj/m$^2$, so the emission intensity of exciting light can be also basically determined within a certain range. The human epithelial tissue varies between individuals, but the overall scope of the emission intensity of exciting light is 0.2 Lux~0.6 Lux. In terms of visual inspection, 0.2 Lux~0.6 Lux is a lower intensity, but it can be visually identified. In specific applications, an equipment, such as endoscope, is needed, since detection and observation need to be performed deeply in human body. When using equipment such as endoscopy, the observed image is actually the image obtained by imaging equipment rather than direct observation of the human eye. For most of the imaging equipments, such as camera, the intensity of 0.2 Lux-0.6 Lux is too low, therefore, the imaging equipments are unable to capture and display the fluorescences. On the other hand, even if such fluorescences can be captured by imaging equipments such as CDD, the signal will be reduced during the process of transmitting the electric signal acquired by CDD to the outside imaging equipment through transmission line of 4 meters, since the endoscope have to be deeply extended into human body, and the length of the endoscope may reach 4 meters. For the fluorescence with an intensity of 0.2 Lux~0.6 Lux, its electric signal is also weak. The attenuation during the transmission process will cause serious distortion to signals and led to deviation of imaging or even no imaging. Taking the requirements on light intensity of imaging equipments in practical application into consideration, the present invention provides an optical observation equipment.

Figure 3:
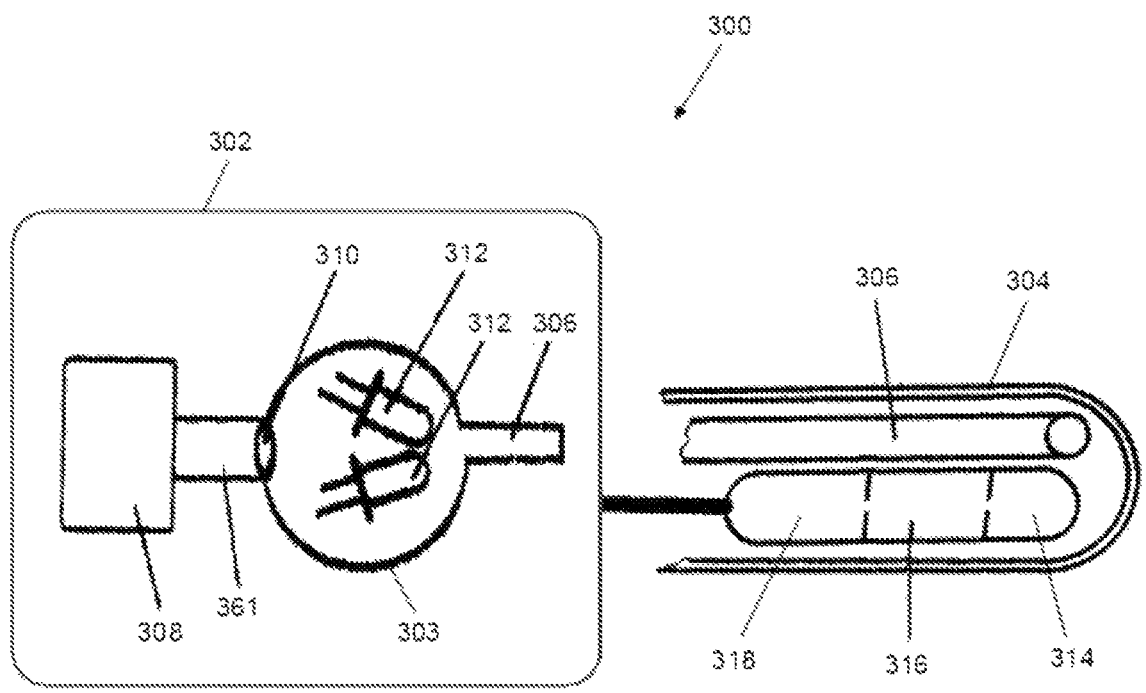
FIG. 3 shows a schematic diagram of the structure of the optical observation equipment according to one embodiment of the present invention.

As shown in FIG. 3, the present invention provides an optical observation equipment for identifying the forming process of a malignant tumor, and the optical observation equipment 300 is provided with a receiving space 302 and a transparent front end 304. The optical observation equipment 300 comprises: a light-guide fiber 306, a laser emitter 308, a focusing device 310, a white light emitter 312, an image sensor 314, a high-gain amplifier 316 and an encoding and emitting device 318.

The input end of light-guide fiber 306 extends to the receiving space 302 and the output end of light-guide fiber 306 extends to the transparent front end 304. The light-guide fiber 306 needs to transmit the laser with a wave band of 340 nm±20 nm and the white light (solar spectrum), therefore, the light-guide fiber 306 should possess a low decay rate in these wave band. In one embodiment, the light-guide fiber 306 is quartz light-guide fiber or liquid light-guide fiber which is suitable for the transmission of ultraviolet band and visible band. In one embodiment, the light-guide fiber shows low decay rate in the wave band range from 300 nm to 700 nm.

The laser emitter 308 is disposed in the receiving space 302 and emits laser with a wavelength of 340 nm±20 nm and an energy of 0.3~0.5 mj/m$^2$ in a pulsing mode. In one embodiment, the laser emitter 308 has a rated output energy >10 mj, a output pulse width <5 ns, a single pulse power >100 KW, and a repeat frequency of 1~50 times/s.

The focusing device 310 is disposed in the receiving space 302 and coupled to the output end of the laser emitter 308, and the focusing device 310 focuses the laser emitted by the laser emitter 308 to the input end of the light-guide fiber 306. In the embodiment shown in FIG. 3, a container 303 is disposed in the receiving space 302 and the container 303 is used for disposing the white light emitter 312. The output end of laser transmitter 308 is firstly coupled to the input end of light-guide fiber 361. In one embodiment, the material of light-guide fiber 361 is identical with that of light-guide fiber 306. In one embodiment, the light-guide fiber 361 may only show low decay rate to the laser with a wave band of 340 nm±20 nm. The output end of light-guide fiber 361 is connected to the container 303, and the focusing device 310 (a focusing mirror) is disposed on the output end of light-guide fiber 361. The focusing direction of focusing device 310 is aligned with on the input end of light-guide fiber 306. The focusing device 310 focuses the laser emitted by the laser emitter 308 to the light-guide fiber 306.

The white light emitter 312 is disposed in the receiving space 302. In the embodiment shown in figures, the white light emitter 312 is disposed in the container 303. The white light emitter 312 is one or several LED (s), and the LED is aligned with the input end of the light-guide fiber 306. The spectrum of LED is a solar spectrum with a color temperature of 5000K±400K. In the embodiment shown in figures, two LEDs (the white light emitter 312) are disposed in the container 303 with a certain angle, and the angle make the LEDs align with the input end of the light-guide fiber 306. The white light emitter 312 emits white light (or sunlight), and the white light is imported into the input end of light-guide fiber 306. In actual use, the laser emitter 308 and the white light emitter 312 are alternately turned on. The white light emitted by white light emitter is used for preliminary observation and screening. The laser emitted by laser emitter is used for exciting fluorescence for identification. The white light emitter should be turned off when a laser is used to excite fluorescence for not affecting the observation of fluorescence, since the intensity of excited fluorescence is relatively low and the intensity of white light is relatively high.

Image sensor 314 is disposed in the transparent front end 304. The image sensor 314 is used for acquiring the image of the area irradiated by light emitted from the output end of the light-guide fiber 306. The image sensor 314 converts light signal into electric signal. In one embodiment, the intensity of excited fluorescence is relatively low, at 0.2 lux~0.6 lux, so a graphene photosensitive element is used in the image sensor 314, which can perceive the fluorescence with an intensity of 0.2 lux~0.6 lux.

The high-gain amplifier 316 is coupled to the image sensor 314 and it is used for amplifying the electric signal generated by the image sensor 314.

The encoding and emitting device 318 is coupled to the high-gain amplifier 316 and it is used for encoding the output from the high-gain amplifier 316 and emitting the encoded signal. In the embodiment, the image sensor 314, the high-gain amplifier 316 and the encoding and emitting device 318 are disposed together and all of them are located in the transparent front end 304, so that the losses during signal transmission between the image sensor 314, the high-gain amplifier 316 and the encoding and emitting device 318 can be reduced or even avoided. The signal acquired by image sensor 314 is amplified and encoded, and then emitted in an encoded mode. According to the prior art, the transmission of encoded image signal can reach a far distance no matter by the way of wire transmission or wireless transmission, the loss during the process of transmission is very small, and the signal can be restored to clear image at the receiving end. An important characteristic of the optical observation equipment of present invention is that the acquired image is firstly encoded, and then transmitted as an encoded signal, so that the back-end coding method that commonly employed in the prior art can be changed, and the losses of electric signal generated by the image sensor during transmission process can be avoided. It should be noted that the image sensor 314, the high-gain amplifier 316 and the encoding and emitting device 318 are commercially available equipments, which can be purchased from the market according to specific parameter requirements. Only the parameters are emphasized herein.

The encoded signal emitted by the encoding and emitting device 318 is received by a receiving and decoding device (not shown in the figure). The encoded signal is decoded by the receiving and decoding device and then provided to a image processing device (not shown in the figure). The image processing device restores the image acquired by the image sensor and displays the image. The coding and decoding of image signal can be achieved using the existing image processing and transmission technology, which is not necessary to be described herein.

Endoscope

Figure 4:
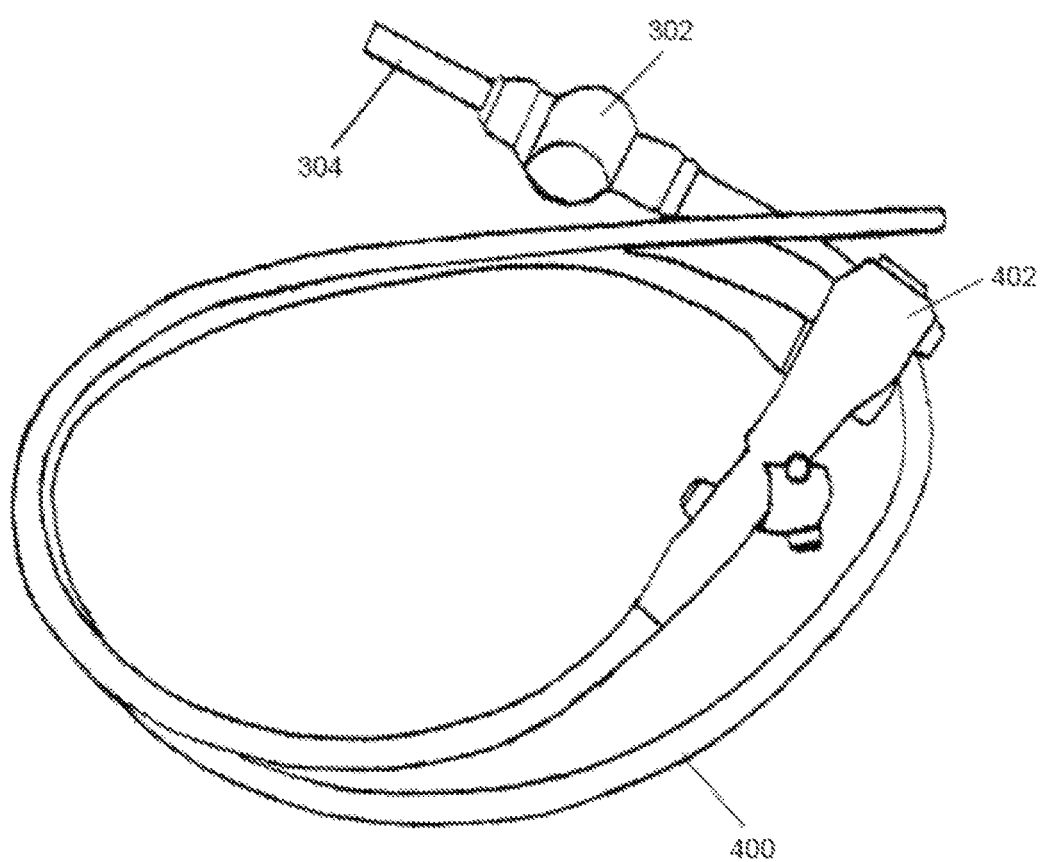
FIG. 4 shows a schematic diagram of the structure of the endoscope according to one embodiment of the present invention.

FIG. 4 shows a schematic diagram of the structure of endoscope in one embodiment of the present invention. As shown in FIG. 4, the present invention also provides an endoscope for identifying the forming process of a malignant tumor. In the front end of endoscope 400, there is the above mentioned optical observation equipment 300. Moreover, the receiving space 302 and the transparent front end 304 are formed in endoscope 400. The endoscope 400 further includes an image processing terminal 402. In the embodiment shown in figures, the image processing terminal 402 is formed on the back end of the endoscope. The image processing terminal 402 includes a receiving and decoding device, an image processing device and a display. The encoded signal emitted by the encoding and emitting device is received and decoded by the receiving and decoding device, and then provided to a image processing device which restores the image acquired by the image sensor and displays the image in the display. The process of coding, transmission, decoding and restoration of image can be achieved by existing technology, which is not repeated here. When the image processing terminal 402 is integrated on the back end of the endoscope, a wired mode can be used in the signal transmission between "encoding and emitting device" and "receiving and decoding device", such as transmission by cable or optical fiber.

In other embodiments, the image processing terminal 402 can also be separated from the main body of endoscope. The image processing terminal can be a separate device. The advantage of this setting is that a larger display can be installed. If separate setting is employed, a wireless mode can be used in the signal transmission between "encoding and emitting device" and "receiving and decoding device".

Alternatively, two image processing terminals can be set, that is, an image processing terminal is installed on the back end of the endoscope and a smaller display is equipped for the direct observation of the operating doctor. And another image processing terminal is installed in a separate position and a bigger display is equipped for the observation of other doctor.

Identification Method

The present invention also provides an method for identifying the forming process of a malignant tumor by using the above mentioned endoscope, the method comprising:

calibrating the laser emitter, wherein the output energy and output frequency of exciting light should be firstly calibrated to ensure clinical application, and the energy of laser reaching the tissue to be tested should be within 0.3~0.5 mj/m$^2$ in the clinical application. The calibration step of laser emitter comprises turning on the laser emitter, adjusting the laser emitter to a state of mono-pulse output, inserting a laser energy meter to detect the output energy of the laser emitter, calibrating the output energy to 2 mj/s and setting the working frequency to 50 times/s.

Stretching the endoscope into a human body, and letting the front end of endoscope reach the area of tissue to be detected.

Turning off the laser emitter, turning on the white light emitter, and irradiating the tissue to be detected with a white light emitted from the output end of the light-guide fiber.

Displaying the image of the tissue to be detected which is irradiated by the white light in a display via the image sensor, the high-gain amplifier, the encoding and emitting device, the receiving and decoding device and the image processing device, and identifying suspected tissue area. Under the irradiation of white light, the general morphologic changes of tissues are observed through the display of image processing terminal. The preliminary judgment of tissues is still performed based on morphology in this step. And the suspected tissue area that is suspected of the existence of lesions is identified.

Turning off the white light emitter, turning on the laser emitter, and irradiating the suspected tissue area with a laser emitted from the output end of the light-guide fiber in a pulse mode.

Displaying the fluorescence image of the suspected tissue area which is irradiated by the laser in the display via the image sensor, the high-gain amplifier, the encoding and emitting device, the receiving and decoding device and the image processing device.

Identifying whether or not the suspected area is relevant to malignant tumor according to the fluorescence color, wherein the peak value of energy at 460 nm±20 nm of normal tissue is used as a reference, if the peak value at 460 nm±20 nm is 100% of the reference value, there is no other peak values, and the fluorescence color is blue and white, the tissue is identified as normal tissue;

if the peak value at 460 nm±20 nm is more than 60% of the reference value, there is no other peak values, and the fluorescence color is orange or orange red, the tissue is identified as benign lesion tissue;

if the peak value at 460 nm±20 nm is less than 40% of the reference value, there are peak values at 400 nm±20 nm and 670 nm±20 nm, and the fluorescence color is violet red, the tissue is identified as malignant tumor tissue;

if the peak value at 460 nm±20 nm is less than 40% of the reference value, there is peak value at 400 nm±20 nm, and the fluorescence color is violet, the tissue is identified as severe atypical hyperplasia tissue;

if the peak value at 460 nm±20 nm is less than 40% of the reference value, there is peak value at 670 nm±20 nm, and the fluorescence color is dark red, the tissue is identified as severe atypical hyperplasia tissue;

if the peak value at 460 nm±20 nm is less than 40% of the reference value, there is no other peak values, and the fluorescence color is dark color, the tissue is identified as mild or moderate atypical hyperplasia tissue.

When irradiating the suspected tissue area with the laser emitter, the scope of irradiation can be properly enlarged to avoid the shortcomings in the existing morphology-based identification method. That is, the area surrounding suspected tissue is also irradiated with a laser. Those areas is probably in a state of precancerous lesion, which may be easily identified as normal tissues by traditional morphological judgment, while can be judged whether or not it belongs to atypical hyperplasia based on fluorescence spectrum through laser irradiation.

For the tissues identified as malignant tumor, severe atypical hyperplasia and mild or moderate atypical hyperplasia through fluorescence spectrum, physiology section should be taken for more accurate pathological diagnosis.

The present invention also provides an method for identifying the forming process of a malignant tumor using the above mentioned optical observation equipment rather than endoscope. The application field of this optical observation equipment is broader than that of the endoscope. For some tissues, such as oral cavity, cervix, anus and rectum which can be easily and directly observed, the optical observation equipment can be directly used for irradiation. Alternatively, the optical observation equipment can be used to directly irradiate and observe tissues which can be directly observed during the process of a surgical operation. As mentioned above, in terms of visual inspection, 0.2 Lux~0.6 Lux is a lower intensity, however it can be visually identified. Therefore, the fluorescence can be directly observed by visual inspection without using imaging equipment in the place of direct observation.

The method comprises:

aligning the transparent front end of the optical observation equipment with a tissue to be detected.

Turning off the laser emitter, turning on the white light emitter, and irradiating the tissue to be detected using the white light emitted from the output end of the light-guide fiber.

Displaying the image of the tissue to be detected which is irradiated by the white light in a display via the image sensor, the high-gain amplifier, the encoding and emitting device, the receiving and decoding device and the image processing device, and identifying suspected tissue area. It can also suitably be directly observed by visual inspection, without using the image sensor, the high-gain amplifier, the encoding and emitting device, the receiving and decoding device and the image processing device.

Turning off the white light emitter, turning on the laser emitter, and irradiating the suspected tissue area using the laser emitted from the output end of the light-guide fiber in a pulse mode.

Displaying the fluorescence image of the suspected tissue area which is irradiated by the laser in the display via the image sensor, the high-gain amplifier, the encoding and emitting device, the receiving and decoding device and the image processing device. The fluorescence image can also suitably be directly observed by visual inspection, without using the image sensor, the high-gain amplifier, the encoding and emitting device, the receiving and decoding device and the image processing device.

Identifying whether or not the suspected area is relevant to malignant tumor according to the fluorescence color, wherein the peak value of energy at 460 nm±20 nm of normal tissue is used as a reference, if the peak value at 460 nm±20 nm is 100% of the reference value, there is no other peak values, and the fluorescence color is blue and white, the tissue is identified as normal tissue;

if the peak value at 460 nm±20 nm is more than 60% of the reference value, there is no other peak values, and the fluorescence color is orange or orange red, the tissue is identified as benign lesion tissue;

if the peak value at 460 nm±20 nm is less than 40% of the reference value, there are peak values at 400 nm±20 nm and 670 nm±20 nm, and the fluorescence color is violet red, the tissue is identified as malignant tumor tissue;

if the peak value at 460 nm±20 nm is less than 40% of the reference value, there is a peak value at 400 nm±20 nm, and the fluorescence color is violet, the tissue is identified as severe atypical hyperplasia tissue;

if the peak value at 460 nm±20 nm is less than 40% of the reference value, there is a peak value at 670 nm±20 nm, and the fluorescence color is dark red, the tissue is identified as severe atypical hyperplasia tissue;

if the peak value at 460 nm±20 nm is less than 40% of the reference value, there is no other peak values, and the fluorescence color is dark color, the tissue is identified as mild or moderate atypical hyperplasia tissue;

The optical observation equipment, the endoscope using the optical observation equipment and the related identification method of the present invention can identify the tumors in stage of precancerous lesion, especially the malignant tumors with lesions smaller than 5 mm in time, i.e., the malignant tumors in the forming process.

EXAMPLE

There are two methods for qualitative identification of epithelial tissue lesions lighted by intrinsic fluorescence, namely fluorescence spectroscopy and intrinsic fluorescence color imaging. The advantage of fluorescence spectroscopy is that it can record a fluorescence spectrum curve, which is convenient for quantitative analysis of NADH, porphyrin and sensitized fluorescence, and its disadvantage is that its sampling point depends on the doctor's experience. However, the fluorescent color image method does not require the doctor's sample experience. Because the fluorescence spectrum curves of various lesions of epithelial tissue are implemented in the visible light band, and the visible light band contains seven-color light of red, orange, yellow, green, blue, indigo, and purple. The fluorescent color imaging directly displays various types of epithelial lesions in different color for qualitative identification.

Figure 7:
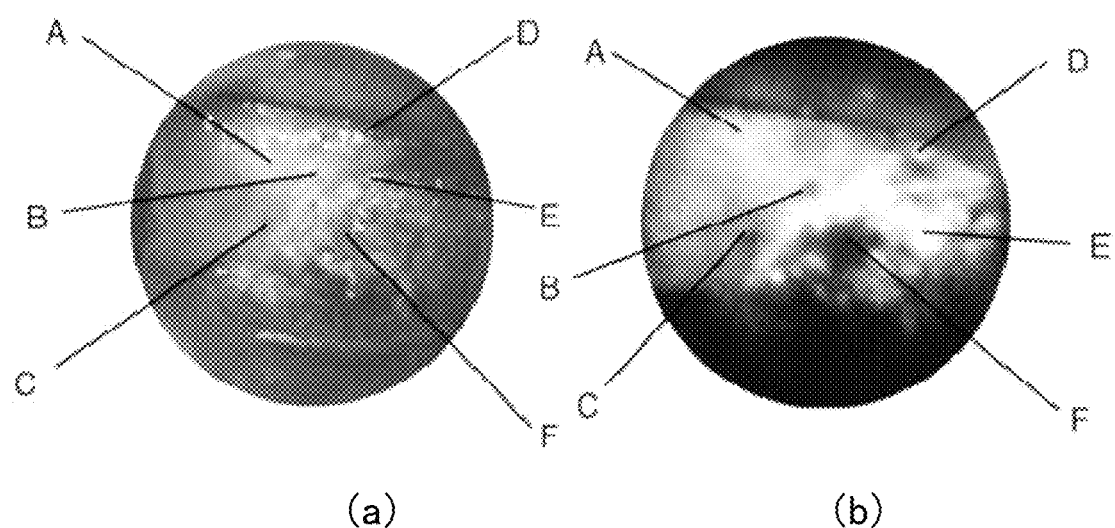
FIG. 7, (a) shows a white light image of a patient with cervical cancer, and (b) shows a fluorescent color image of a patient with cervical cancer according to one embodiment of the present invention.

In FIG. 7, (a) is a white light image of a patient with cervical cancer, and (b) is a fluorescent color image of a patient with cervical cancer. From the visual detection of white light image, generally experienced gynecological oncologists can diagnose cervical cancer. The surface layer of cervical cancer has been covered with a layer of yellow necrotic tissue. But from the fluorescence image on the right, four different epithelial tissues can be distinguished by color.

In FIG. 7, (A) is a normal epithelial tissue far away from the cancer, and its fluorescent color is off-blue, and the proportion of the three colors (red, green, blue) corresponding to off-blue is (85%, 100%, 100%);

(B) is a severe atypical hyperplasia tissue close to the cancer tissue, and its fluorescent color is violet, and the proportion of the three colors (red, green, blue) corresponding to violet is (40%, 0%, 40%);

(C) is also a severe atypical hyperplasia tissue close to the cancer tissue, and its fluorescent color is also violet, and the proportion of the three colors (red, green, blue) corresponding to violet is (40%, 0%, 40%);

(D) is the surface of cervical cancer epithelial tissue covered with a layer of necrotic tissue (necrotic tissue is benign lesion tissue), and its fluorescent color is orange, and the proportion of the three colors (red, green, blue) corresponding to orange is (100%, 60%, 20%);

(E) is also a necrotic tissue, and its fluorescent color is also orange, and the proportion of the three colors (red, green, blue) corresponding to orange is (100%, 60%, 20%);

(F) is the epithelial tissue of cervical cancer, and its fluorescent color is violet red, and the proportion of the three colors (red, green, blue) corresponding to violet red is (80%, 0%, 60%).

The above mentioned embodiments are provided to the skilled person in the art for realizing or using the present invention. The skilled person can make various modifications or amendments to the above mentioned embodiments without departing from the ideas of the present invention. Therefore, the protection scope of the present invention is not limited by the above mentioned embodiments, while should be the maximum scope conforming with the innovative features referred by the claims.

The invention claimed is:

1. A method for identifying a formation process of a malignant tumor, wherein the method comprises:

Step 1: providing an optical observation equipment for identifying the forming process of the malignant tumor, wherein the optical observation equipment has a receiving space and a transparent front end, and the optical observation equipment comprises:

a light-guide fiber, an input end of which extends to the receiving space and an output end of which extends to the transparent front end;

a laser emitter, which is disposed in the receiving space and emits laser light with a wavelength of 340 nm±20 nm and an energy in a range from 0.3mj/m$^2$ to 0.5mj/m$^2$ in a pulsing mode;

a focusing device comprising a focusing mirror, which is disposed in the receiving space and coupled to an output end of the laser emitter, and which is used for focusing the laser light to the input end of the light-guide fiber;

a white light emitter, which is disposed in the receiving space and emits white light, and the white light is guided into the input end of the light-guide fiber;

an image sensor, which is disposed in the transparent front end, and which is configured to be used for acquiring an image of an area irradiated by the white or the laser light emitted from the output end of the light-guide fiber and converting a light signal into an electric signal; and a gain amplifier, which is coupled to the image sensor and is used for amplifying the electric signal generated by the image sensor;

Step 2: aligning the transparent front end of the optical observation equipment with a tissue to be detected;

Step 3: irradiating the tissue to be detected with a white light emitted from the output end of the light-guide fiber;

Step 4: displaying an image of the tissue to be detected which is irradiated by the white light in a display, and identifying a suspected tissue area;

Step 5: irradiating the suspected tissue area with the laser light emitted from the output end of the light-guide fiber in a pulse mode;

Step 6: displaying a fluorescence image of the suspected tissue area which is irradiated by the laser light in the display, and obtaining a fluorescence spectrum of the tissue, wherein the fluorescence spectrum generated is all in the visible light band of 400 nm-700 nm;

Step 7: identifying whether or not the suspected tissue area is relevant to the malignant tumor formation on the basis of the fluorescence spectrum, wherein a peak value at 460 nm=20 nm of a fluorescence spectrum of a normal tissue is used as a reference value, and wherein the identifying whether or not the suspected tissue area is relevant to the malignant tumor formation on the basis of the fluorescence spectrum comprises:

determining whether the fluorescence spectrum of the tissue has a peak value at 460 nm±20 nm that is 100% of the reference value, and the fluorescence spectrum of the tissue has no peak values at 400-20 nm and 670+20 nm, thereby identifying whether the tissue is the normal tissue;

determining whether the fluorescence spectrum of the tissue has a peak value at 460 nm±20 nm that is more than 60% of the reference value, and the fluorescence spectrum of the tissue has no peak values at 400-20 nm and 670±20 nm of the fluorescence spectrum, thereby identifying whether the tissue is a benign lesion tissue;

determining whether the fluorescence spectrum of the tissue has a peak value at 460 nm±20 nm that is less than 40% of the reference value, and the fluorescence spectrum of the tissue has peak values at 400 nm±20 nm and 670 nm±20 nm, thereby identifying whether the tissue is the malignant tumor tissue;

determining whether the fluorescence spectrum of the tissue has a peak value at 460 nm±20 nm that is less than 40% of the reference value, the fluorescence spectrum of the tissue has a peak value at 400 nm±20 nm, and the fluorescence spectrum of the tissue has no peak value at 670 nm±20 nm, thereby identifying whether the tissue is identified as a severe atypical hyperplasia tissue;

determining whether the fluorescence spectrum of the tissue has a peak value at 460 nm±20 nm that is less than 40% of the reference value, the fluorescence spectrum of the tissue has a peak value at 670 nm±20 nm, and the fluorescence spectrum of the tissue has no peak value at 400 nm±20 nm, thereby identifying whether the tissue is identified as a severe atypical hyperplasia tissue; and determining whether the fluorescence spectrum of the tissue has a peak value at 460 nm±20 nm that is less than 40% of the reference value, and the fluorescence spectrum of the tissue has no peak values at 400 nm±20 nm and 670 nm±20 nm, thereby identifying whether the tissue is identified as a mild or moderate atypical hyperplasia tissue;

Step 8: mapping a curve profile of the fluorescence spectrum of the tissue as a fluorescence chromatographic energy diagram, wherein the fluorescence chromatographic energy diagram is a color image in which different wavelengths of the fluorescence spectrum are mapped to specific colors including at least one of red, orange, yellow, green, blue, indigo, purple, and wherein a whole spectrum band of 400 nm-700 nm is distributed in the visible light band, an intensity of a peak represents an intensity of a color, and peak values of different wavelengths exhibit different colors, so that doctors can directly identify a nature of a lesion according to fluorescent color of the lesion through visual method.

2. The method according to claim 1, wherein the laser emitter has an output pulse width <5 ns and a repeat frequency of 1~50 times/s.

3. The method according to claim 1, wherein the white light emitter is one or several light-emitting diodes which are aligned with the input end of the light-guide fiber, and have a solar spectrum with a color temperature of 5000K±400K.

4. The method according to claim 1, wherein the light-guide fiber is a quartz light-guide fiber or a liquid light-guide fiber which is suitable for the transmission of ultraviolet band and visible band; and the light-guide fiber shows a low decay rate within the wavelength range from 300 nm to 700 nm.

5. The method according to claim 1, wherein a graphene photosensitive element is used in the image sensor, which can perceive a fluorescence with an intensity of 0.2 lux to 0.6lux.

6. A method for identifying a formation process of a malignant tumor, wherein the method comprises:

Step 1: providing an endoscope for identifying the formation process of the malignant tumor, wherein the endoscope comprises an optical observation equipment for identifying the forming process of the malignant tumor, and the optical observation equipment is located at the front end of the endoscope, the optical observation equipment has a receiving space and a transparent front end, and the optical observation equipment comprises:

a light-guide fiber, an input end of which extends to the receiving space and an output end of which extends to the transparent front end;

a laser emitter, which is disposed in the receiving space and emits laser light with a wavelength of 340 nm±20 nm and an energy in a range from 0.3mj/m² to 0.5mj/m² in a pulsing mode;

a focusing device comprising a focusing mirror, which is disposed in the receiving space and coupled to an output end of the laser emitter, and which is used for focusing the laser light to the input end of the light-guide fiber;

a white light emitter, which is disposed in the receiving space and emits white light, and the white light is guided into the input end of the light-guide fiber;

an image sensor, which is disposed in the transparent front end, and which is configured to be used for acquiring an image of an area irradiated by the white or the laser light emitted from the output end of the light-guide fiber and converting a light signal into an electric signal; and a gain amplifier, which is coupled to the image sensor and is used for amplifying the electric signal generated by the image sensor;

Step 2: placing the endoscope into a human body, and letting the front end of endoscope reach the position of tissue to be detected;

Step 3: irradiating the tissue to be detected with a white light emitted from the output end of the light-guide fiber;

Step 4: displaying an image of the tissue to be detected which is irradiated by the white light in a display, and identifying suspected tissue area;

Step 5: irradiating the suspected tissue area with the laser light emitted from the output end of the light-guide fiber in a pulse mode;

Step 6: displaying a fluorescence image of the suspected tissue area which is irradiated by the laser light in the display, and obtaining a fluorescence spectrum of the suspected tissue area, wherein the fluorescence spectrum generated is all in the visible light band of 400 nm-700 nm;

Step 7: identifying whether or not the suspected tissue area is relevant to the malignant tumor formation according to the fluorescence spectrum, wherein a peak value at 460 nm±20 nm of a fluorescence spectrum of a normal tissue is used as a reference value, and wherein the identifying whether or not the suspected tissue area is relevant to the malignant tumor formation according to the fluorescence spectrum comprises:

determining whether the fluorescence spectrum of the tissue has a peak value at 460 nm±20 nm that is 100% of the reference value, and the fluorescence spectrum of the tissue has no peak values at 400±20 nm and 670±20 nm, thereby identifying whether the tissue is as the normal tissue;

determining whether the fluorescence spectrum of the tissue has a peak value at 460 nm±20 nm that is more than 60% of the reference value, and the fluorescence spectrum of the tissue has no peak values at 400±20 nm and 670±20 nm of the fluorescence spectrum, thereby identifying whether the tissue a benign lesion tissue;

determining whether the fluorescence spectrum of the tissue has a peak value at 460 nm±20 nm that is less than 40% of the reference value, and the fluorescence spectrum of the tissue has peak values at 400 nm±20 nm and 670 nm±20 nm, thereby identifying whether the tissue is the malignant tumor tissue;

determining whether the fluorescence spectrum of the tissue has a peak value at 460 nm±20 nm that is less than 40% of the reference value, the fluorescence spectrum of the tissue has a peak value at 400 nm±20 nm, and the fluorescence spectrum of the tissue has no peak value at 670 nm±20 nm, thereby identifying whether the tissue is identified as a severe atypical hyperplasia tissue;

determining whether the fluorescence spectrum of the tissue has a peak value at 460 nm±20 nm that is less than 40% of the reference value, the fluorescence spectrum of the tissue has a peak value at 670 nm±20 nm, and the fluorescence spectrum of the tissue has no peak value at 400 nm±20 nm, thereby identifying whether the tissue is identified as a severe atypical hyperplasia tissue; and determining whether the fluorescence spectrum of the tissue has a peak value at 460 nm±20 nm that is less than 40% of the reference value, and the fluorescence spectrum of the tissue has no peak values at 400 nm±20 nm and 670 nm±20 nm, thereby identifying whether the tissue is identified as a mild or moderate atypical hyperplasia tissue;

Step 8: mapping a curve profile of the fluorescence spectrum of the tissue as a fluorescence chromatographic energy diagram, wherein the fluorescence chromatographic energy diagram is a color image in which different wavelengths of the fluorescence spectrum are mapped to specific colors including at least one of red, orange, yellow, green, blue, indigo, purple, and wherein a whole spectrum band of 400 nm-700 nm is distributed in the visible light band, an intensity of a peak represents an intensity of a color, and peak values of different wavelengths exhibit different colors, so that doctors can directly identify a nature of a lesion according to fluorescent color of the lesion through visual method.

7. The method according to claim 6, wherein the laser emitter has an output pulse width <5 ns and a repeat frequency of 1~50 times/s.

8. The method according to claim 6, wherein the white light emitter is one or several light-emitting diodes which are aligned with the input end of the light-guide fiber, and have a solar spectrum with a color temperature of 5000K±400K.

9. The method according to claim 6, wherein the light-guide fiber is a quartz light-guide fiber or a liquid light-guide fiber which is suitable for the transmission of ultraviolet band and visible band; and the light-guide fiber shows a low decay rate within the wavelength range from 300 nm to 700 nm.

10. The method according to claim 6, wherein a graphene photosensitive element is used in the image sensor, which can perceive a fluorescence with an intensity of 0.2 lux to 0.6lux.

11. The method according to claim 6, wherein the endoscope also comprises an image processing terminal located at an end of the endoscope.

* * * * *